United States Patent
Reif et al.

(10) Patent No.: US 10,874,114 B2
(45) Date of Patent: Dec. 29, 2020

(54) SUPPLEMENTATION OF MILK FORMULAS WITH MICROVESICLES ISOLATED FROM MILK

(71) Applicant: HADASIT MEDICAL RESEARCH SERVICES AND DEVELOPMENT LTD., Jerusalem (IL)

(72) Inventors: Shimon Reif, Jerusalem (IL); Regina Golan, Maale Michmash (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 235 days.

(21) Appl. No.: 15/778,993

(22) PCT Filed: Nov. 29, 2016

(86) PCT No.: PCT/IL2016/051277
§ 371 (c)(1),
(2) Date: May 24, 2018

(87) PCT Pub. No.: WO2017/090049
PCT Pub. Date: Jun. 1, 2017

(65) Prior Publication Data
US 2018/0343882 A1    Dec. 6, 2018

Related U.S. Application Data

(60) Provisional application No. 62/260,546, filed on Nov. 29, 2015.

(51) Int. Cl.
| | |
|---|---|
| *A23C 9/15* | (2006.01) |
| *A23C 9/20* | (2006.01) |
| *C12N 15/113* | (2010.01) |
| *C12N 15/11* | (2006.01) |
| *A23L 33/13* | (2016.01) |
| *A23L 33/00* | (2016.01) |
| *A61P 35/00* | (2006.01) |
| *A61K 9/127* | (2006.01) |
| *A61K 31/7105* | (2006.01) |

(52) U.S. Cl.
CPC .......... *A23C 9/1512* (2013.01); *A23C 9/20* (2013.01); *A23L 33/13* (2016.08); *A23L 33/40* (2016.08); *A61K 9/1276* (2013.01); *A61K 31/7105* (2013.01); *A61P 35/00* (2018.01); *C12N 15/111* (2013.01); *C12N 15/113* (2013.01); *A23C 2240/05* (2013.01); *A23V 2002/00* (2013.01); *A23V 2250/18* (2013.01); *C12N 2310/141* (2013.01); *C12N 2320/32* (2013.01)

(58) Field of Classification Search
CPC ..... A23C 9/1512; A23C 9/20; A23C 2240/05; C12N 15/113; C12N 15/111; C12N 2310/141; C12N 2320/32; A23L 33/13; A23L 33/40; A61P 35/00; A61K 9/1276; A61K 31/7105; A23V 2002/00; A23V 2250/18
USPC ................................................. 424/450, 489
See application file for complete search history.

(56) References Cited

U.S. PATENT DOCUMENTS

| | | | |
|---|---|---|---|
| 2012/0093874 A1 | 4/2012 | Ochiya et al. | |
| 2013/0273544 A1 | 10/2013 | Vlassov et al. | |
| 2014/0302205 A1* | 10/2014 | Melnik ............ | A23C 9/00 426/238 |
| 2016/0000710 A1* | 1/2016 | Gupta ............... | A61K 31/337 424/450 |

FOREIGN PATENT DOCUMENTS

| | | | | |
|---|---|---|---|---|
| EP | 2 455 486 A1 | 5/2012 | | |
| EP | 2 896 294 A1 | 7/2015 | | |
| EP | 2896284 A1 * | 7/2015 | ........... | A01D 57/20 |
| WO | 2014/036726 A1 | 3/2014 | | |
| WO | 2014/134132 A1 | 9/2014 | | |
| WO | WO-2014134132 A1 * | 9/2014 | ......... | A61K 31/704 |

OTHER PUBLICATIONS

Alsaweed et al. Int. J. Environ. Res. Public Health 2015, 12, 13981-14020. (Year: 2015).*
Admyre et al., (2007) Exosomes with immune modulatory features are present in human breast milk. The Journal of Immunology, 179(3), 1969-1978.
Alsaweed et al., (2015) MicroRNAs in breastmilk and the lactating breast: potential immunoprotectors and developmental regulators for the infant and the mother. International journal of environmental research and public health, 12(11), 13981-14020.
Ambros, (2004) The functions of animal microRNAs. Nature, 431(7006), 350-355.
Amitay et al., (2015) Breastfeeding and childhood leukemia incidence: a meta-analysis and systematic review. JAMA pediatrics, 169(6), e151025-e151025.
Baier et al., (2014) MicroRNAs Are Absorbed in Biologically Meaningful Amounts from Nutritionally Relevant Doses of Cow Milk and Affect Gene Expression in Peripheral Blood Mononuclear Cells, HEK-293 Kidney Cell Cultures, and Mouse Livers-3. The Journal of nutrition, 144(10), 1495-1500.
Cortez et al., (2009) MicroRNA identification in plasma and serum: a new tool to diagnose and monitor diseases. Expert opinion on biological therapy, 9(6), 703-711.
De Guire et al., (2010) Designing small multiple-target artificial RNAs. Nucleic acids research, 38(13), e140-e140.
De Oliveira et al., (2012) MicroRNA expression and activity in pediatric acute lymphoblastic leukemia (ALL). Pediatric blood & cancer, 59(4), 599-604.

(Continued)

*Primary Examiner* — Janet L Epps-Smith
(74) *Attorney, Agent, or Firm* — Allan A. Fanucci

(57) ABSTRACT

Provided are microvesicles isolated from milk, compositions thereof and uses for the preparation of milk formulas. Further provided are microvesicles, including exosomes and/or fat globules which encapsulate various miRNA molecules and uses thereof, as exemplified by supplementing milk formulas.

12 Claims, 10 Drawing Sheets

(56) References Cited

OTHER PUBLICATIONS

Dreiucker et al., (2011) Fatty acids patterns in camel, moose, cow and human milk as determined with GC/MS after silver ion solid phase extraction. Food chemistry, 126(2), 762-771.

Elbaum Shiff et al., (2016) Expression of miRNAs related to obesity and diabetes in human milk. 10th Congress of the International Society of Nutrigenetics/Nutrigenomics (ISNN). May 22-26, 2016, Tel Aviv, Israel. J Nutrigenet Nutrigenomics 9: 151-210; p. 177. Abstract.

Escrevente et al., (2011) Interaction and uptake of exosomes by ovarian cancer cells. BMC cancer, 11(1), 108.

Feng et al., (2010) Cellular internalization of exosomes occurs through phagocytosis. Traffic, 11(5), 675-687.

Floris et al., (2015) MiRNA analysis by quantitative PCR in preterm human breast milk reveals daily fluctuations of hsa-miR-16-5p. PloS one, 10(10), e0140488, 1-15.

Garzon et al., (2008) MicroRNA signatures associated with cytogenetics and prognosis in acute myeloid leukemia. Blood, 111(6), 3183-3189.

Golan-Gerstl et al., (2016) Expression and biological function of miRNA in breast milk. 10th Congress of the International Society of Nutrigenetics/Nutrigenomics (ISNN). May 22-26, 2016, Tel Aviv, Israel. J Nutrigenet Nutrigenomics 9: 151-210; p. 164. Abstract.

Ha, (2011) MicroRNAs in human diseases: from cancer to cardiovascular disease. Immune network, 11(3), 135-154.

Hata et al., (2010) Isolation of bovine milk-derived microvesicles carrying mRNAs and microRNAs. Biochemical and biophysical research communications, 396(2), 528-533.

Izumi et al., (2012) Bovine milk contains microRNA and messenger RNA that are stable under degradative conditions. Journal of dairy science, 95(9), 4831-4841.

Izumi et al., (2014) Time-dependent expression profiles of microRNAs and mRNAs in rat milk whey. PloS one, 9(2), e88843 1-13.

Izumi et al., (2015) Bovine milk exosomes contain microRNA and mRNA and are taken up by human macrophages. Journal of dairy science, 98(5), 2920-2933.

Ji et al., (2012) Identification of novel and differentially expressed microRNAs of dairy goat mammary gland tissues using Solexa sequencing and bioinformatics. PloS one, 7(11), e49463.

Johnson et al., (2012) The human microbiome and its potential importance to pediatrics. Pediatrics, 129(5), 950-960.

Kosaka et al., (2010) microRNA as a new immune-regulatory agent in breast milk. Silence, 1(1), 7, 1-8.

Kwan et al., (2004) Breastfeeding and the risk of childhood leukemia: a meta-analysis. Public health reports, 119(6), 521-535.

Lässer et al., (2011) Human saliva, plasma and breast milk exosomes contain RNA: uptake by macrophages. Journal of translational medicine, 9(1), 9, 1-8.

Li at al., (2012) Expression profiles of microRNAs from lactating and non-lactating bovine mammary glands and identification of miRNA related to lactation. BMC genomics, 13(1), 731, 1-15.

Melnik et al., (2014) Milk: an exosomal microRNA transmitter promoting thymic regulatory T cell maturation preventing the development of atopy? Journal of translational medicine, 12(1), 43, 1-11.

Metz et al., (2016) Vitamin A and epigenetics. 10th Congress of the International Society of Nutrigenetics/Nutrigenomics (ISNN). May 22-26, 2016, Tel Aviv, Israel. J Nutrigenet Nutrigenomics 9: 151-210; p. 183. Abstract.

Munch et al., (2013) Transcriptome profiling of microRNA by Next-Gen deep sequencing reveals known and novel miRNA species in the lipid fraction of human breast milk. PLoS One, 8(2), e50564, 1-13.

Niederwieser et al., (2015) Prognostic and biologic significance of DNMT3B expression in older patients with cytogenetically normal primary acute myeloid leukemia. Leukemia, 29(3), 567-575.

Park et al., (2009) miR-29 miRNAs activate p53 by targeting p85a and CDC42. Nature Structural and Molecular Biology, 16(1), 23-29.

Stuebe et al., (2010) the risks and benefits of infant feeding practices for women and their children. Journal of Perinatology, 30(3), 155-162.

Sylvestre et al., (2007) An E2F/miR-20a autoregulatory feedback loop. Journal of Biological Chemistry, 282(4), 2135-2143.

Valadi et al., (2007) Exosome-mediated transfer of mRNAs and microRNAs is a novel mechanism of genetic exchange between cells. Nature cell biology, 9(6), 654-659.

Verhasselt et al., (2008) Breast milk—mediated transfer of an antigen induces tolerance and protection from allergic asthma. Nature medicine, 14(2), 170-175.

Weber et al., (2010) The microRNA spectrum in 12 body fluids. Clinical chemistry, 56(11), 1733-1741.

Wolf et al., (2015) The Intestinal Transport of Bovine Milk Exosomes Is Mediated by Endocytosis in Human Colon Carcinoma Caco-2 Cells and Rat Small Intestinal IEC-6 Cells-3. The Journal of nutrition, 145(10), 2201-2206.

Yamamoto et al., (2012) Oral tolerance induced by transfer of food antigens via breast milk of allergic mothers prevents offspring from developing allergic symptoms in a mouse food allergy model. Clinical and Developmental Immunology, 1-9.

Zhang et al., (2009) MicroRNA patterns associated with clinical prognostic parameters and CNS relapse prediction in pediatric acute leukemia. PloS one, 4(11), e7826, 1-10.

Zhou et al (2012) Immune-related microRNAs are abundant in breast milk exosomes. International journal of biological sciences, 8(1), 118-123.

Arntz et al., (2015) Oral administration of bovine milk derived extracellular vesicles attenuates arthritis in two mouse models. Mol Nutr Food Res 59(9): 1701-1712.

Chen et al., (2013) Decreased miRNA-148a is associated with lymph node metastasis and poor clinical outcomes and functions as a suppressor of tumor metastasis in non-small cell lung cancer. Oncol Rep 30(4): 1832-1840.

Chen et al., (2010) Identification and characterization of microRNAs in raw milk during different periods of lactation, commercial fluid, and powdered milk products. Cell Res 20(10): 1128-1137.

* cited by examiner

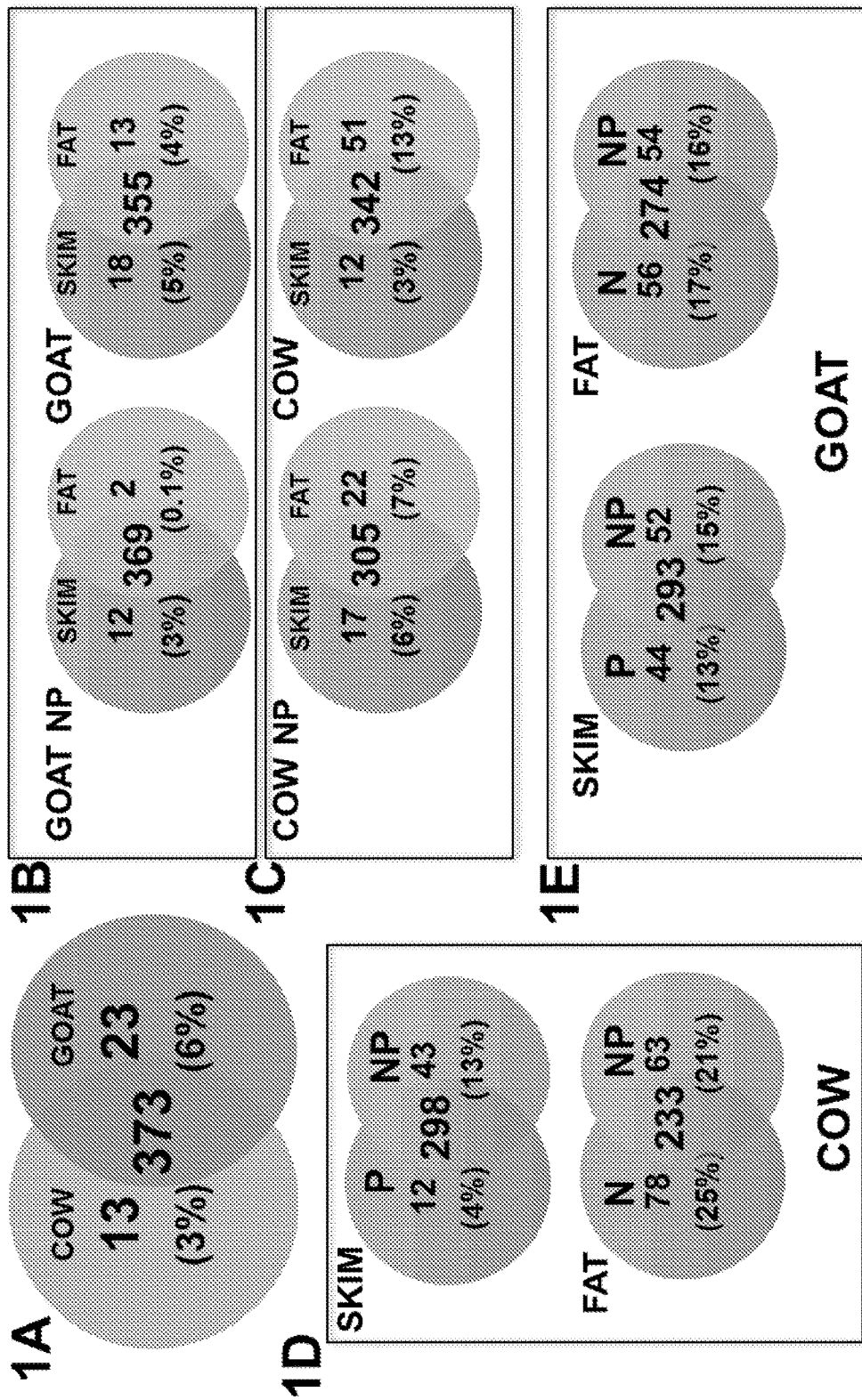
Figs. 1A-E

Fig. 2A cow milk not pasteurized

| SKIM MILK | | FAT | |
|---|---|---|---|
| miRNA | % | miRNA | % |
| miR-148a-3p | 23.26 | miR-148a-3p | 60.53 |
| miR-6073 | 20.40 | miR-30a-5p | 7.72 |
| miR-200c | 5.96 | miR-21-5p | 7.11 |
| miR-200b | 4.11 | miR-6073 | 2.48 |
| miR-99a-5p | 3.91 | miR-26a-5p | 1.54 |
| miR-30a-5p | 3.43 | let-7f-5p | 1.37 |
| miR-30d | 3.24 | let-7g-5p | 1.21 |
| miR-320-3p | 3.23 | miR-99a-5p | 1.19 |
| let-7a-5p | 2.74 | miR-200a | 0.98 |
| miR-26a-5p | 2.53 | miR-22-3p | 0.93 |

Fig. 2B cow milk pasteurized

| SKIM MILK | | FAT | |
|---|---|---|---|
| miRNA | % | miRNA | % |
| miR-148a-3p | 16.09 | miR-6073 | 48.95 |
| miR-6073 | 12.69 | miR-148a-3p | 7.16 |
| miR-200c | 6.52 | miR-30a-5p | 5.15 |
| miR-3135b | 4.62 | miR-21-5p | 4.27 |
| miR-30d | 3.88 | chi-miR-200c | 2.74 |
| let-7b-5p | 3.86 | miR-320-3p | 2.58 |
| let-7a-5p | 3.73 | let-7b-5p | 2.39 |
| miR-200b | 3.44 | miR-200b | 2.26 |
| miR-4492 | 3.35 | miR-26a-5p | 1.70 |
| miR-718 | 3.06 | miR-1246 | 1.62 |

Fig. 2C goat milk not pasteurized

| SKIM MILK | | FAT | |
|---|---|---|---|
| miRNA | % | miRNA | % |
| miR-148a-3p | 43.21 | miR-148a-3p | 60.95 |
| miR-6073 | 6.14 | miR-30a-5p | 5.00 |
| miR-200b | 3.75 | miR-26a | 3.46 |
| miR-200c | 3.60 | miR-21-5p | 3.09 |
| miR-30a-5p | 3.45 | let-7g-5p | 1.89 |
| miR-21-5p | 2.96 | miR-22-3p | 1.35 |
| miR-26a-5p | 2.44 | miR-378-3p | 1.28 |
| miR-30d | 2.29 | miR-146b-5p | 1.25 |
| miR-378-3p | 1.85 | miR-200a | 1.24 |
| miR-146b-5p | 1.71 | miR-30d | 1.18 |

Fig. 2D goat milk pasteurized

| SKIM MILK | | FAT | |
|---|---|---|---|
| miRNA | % | miRNA | % |
| miR-148a-3p | 23.96 | miR-148a-3p | 28.08 |
| miR-6073 | 17.06 | miR-6073 | 8.62 |
| miR-200c | 5.09 | miR-21-5p | 6.68 |
| miR-30d | 5.03 | miR-26a-5p | 4.52 |
| miR-1246 | 4.06 | miR-30a-5p | 3.50 |
| miR-200b | 3.77 | let-7a-5p | 3.10 |
| miR-375 | 3.59 | miR-200c | 2.78 |
| miR-30a-5p | 3.31 | let-7f-5p | 2.53 |
| miR-320-3p | 2.61 | miR-200b | 2.41 |
| miR-146b-5p | 2.57 | let-7b-5p | 2.16 |

Fig. 3A
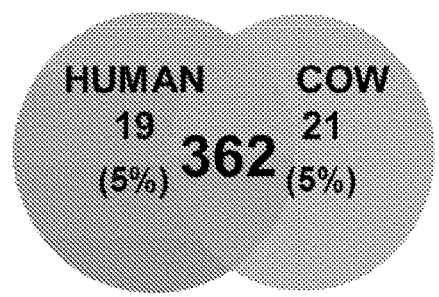
Fig. 3B
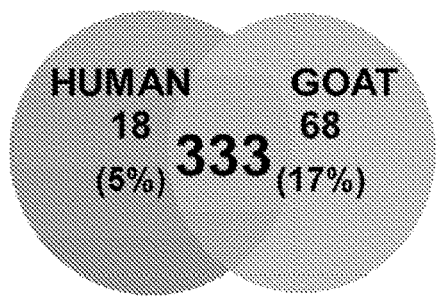
Fig. 3C
Fig. 3D
human milk
| SKIM MILK | | FAT | |
|---|---|---|---|
| miRNA | % | miRNA | % |
| miR-148a-3p | 37.59 | miR-6073 | 30.22 |
| miR-6073 | 11.77 | miR-148a-3p | 7.59 |
| miR-30a-5p | 5.92 | miR-320-3p | 4.48 |
| miR-99a-5p | 3.68 | miR-378-3p | 4.33 |
| miR-146b-5p | 3.51 | miR-146b-5p | 3.60 |
| miR-200a | 3.10 | miR-22-3p | 3.54 |
| miR-21-5p | 2.77 | miR-99a-5p | 3.52 |
| miR-30d | 1.72 | let-7b-5p | 3.21 |
| let-7b-5p | 1.56 | miR-30a-5p | 2.76 |
| let-7a-5p | 1.30 | miR-184 | 2.01 |

FAT COLOSTRUM

WHEY COLOSTRUM

FAT IM

WHEY IM

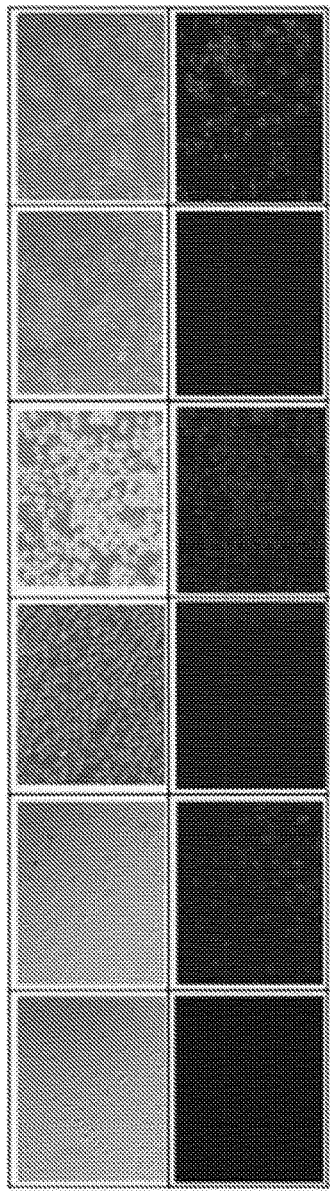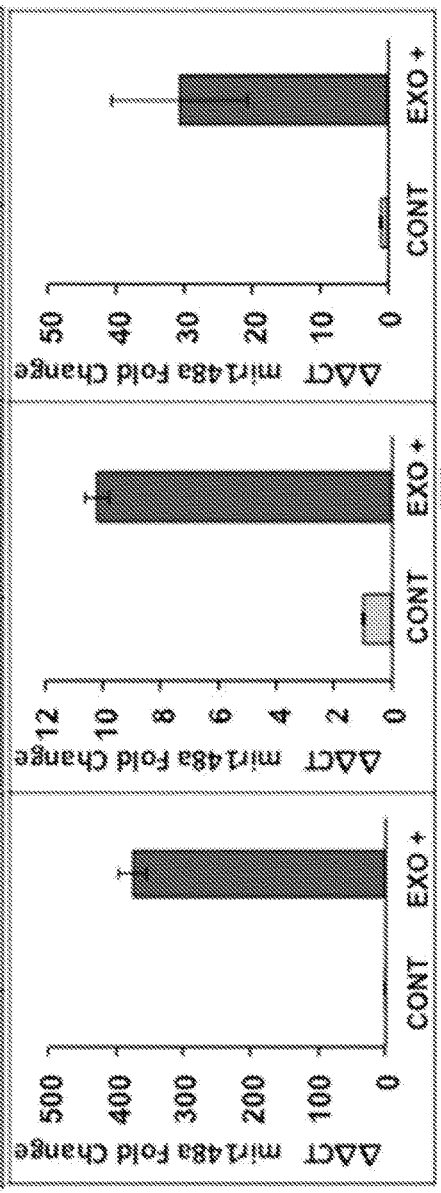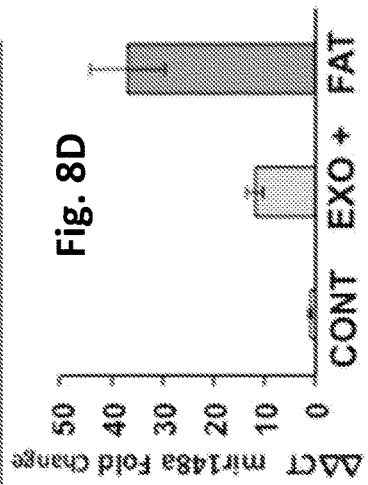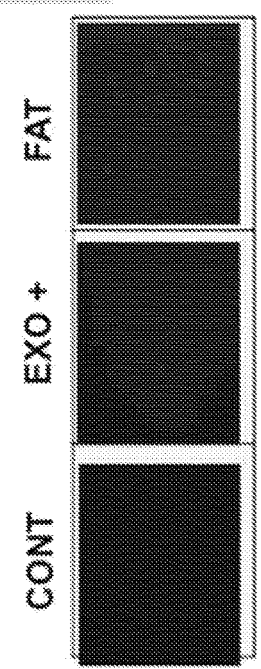
Fig. 8A
Fig. 8B
Fig. 8C
Fig. 8D

Fig. 9A
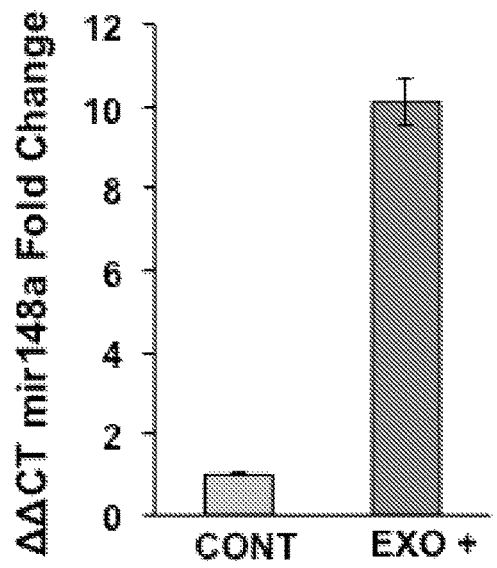
Fig. 9B
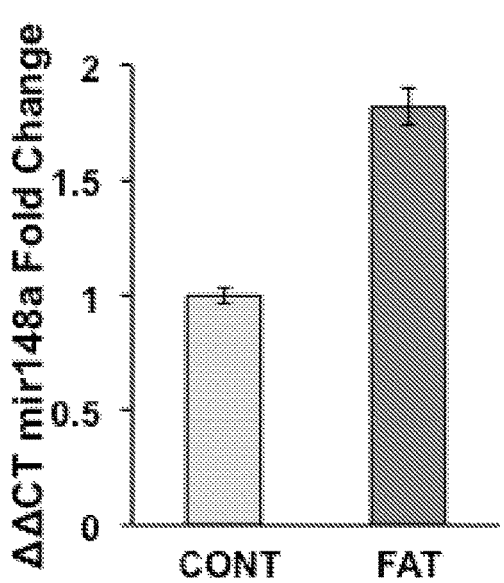
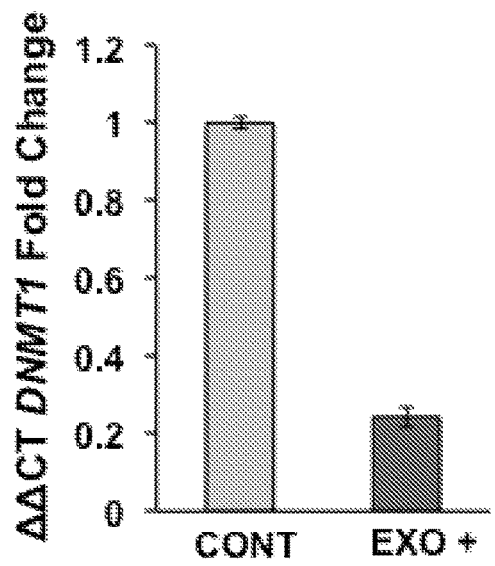
CRL1831
Fig. 9C
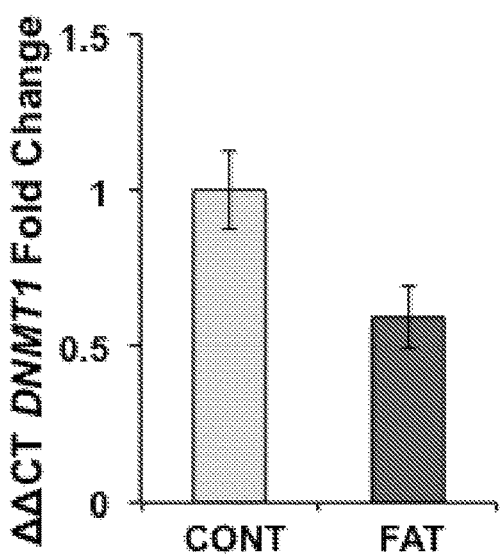
K652
Fig. 9D

Fig. 10A
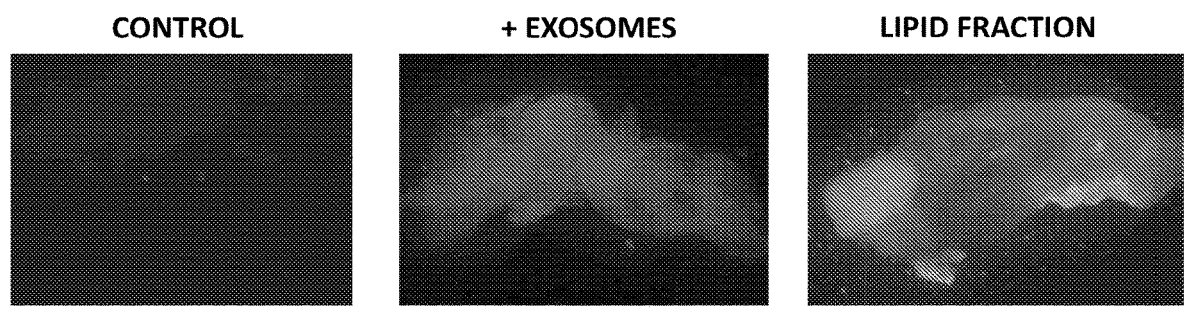
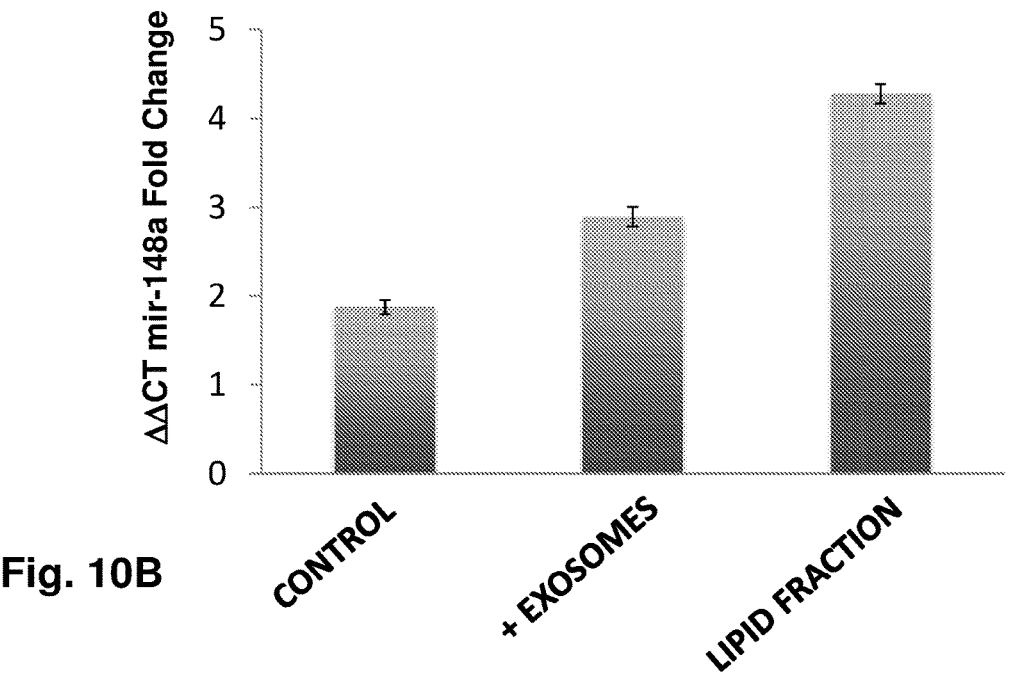
Fig. 10B

SUPPLEMENTATION OF MILK FORMULAS WITH MICROVESICLES ISOLATED FROM MILK

FIELD OF THE INVENTION

The present invention relates to microvesicles (such as, vesicles, exosomes, fat globules and the like) isolated from milk uses thereof in milk formulas.

BACKGROUND OF THE INVENTION

Milk is a main nutritional source for newborn mammals and breastfeeding is recognized as one of the most valuable contributors to infant health to adequate growth of the brain and the immune system. Moreover, there are evidences to support that breastfeeding protects from neonatal necrotizing enterocolitis and other infections. Milk components have been reported to exert biological effects on the neonatal small intestine and neonatal intestinal epithelial cells and provide protection against early infections in neonates. Moreover, various epidemiological studies have demonstrated that breastfeeding can reduce the rate of childhood leukemia by approximately 20%.

Other studies, have demonstrated that mammalian milk contains exosomes, which have the ability to transfer biological macromolecules (such as miRNA) intracellularly by fusion. Micro RNA are small RNAs involved in post transcriptional regulation of targets RNAs and play crucial role in regulating a wide range of cellular functions such as cell differentiation, proliferation and cell death. miRNA has been associated with the development and progression of different malignancies, including leukemia. Milk miRNAs were found to be stable to acidic conditions and resistant to RNase or freeze-thaw cycle degradation.

International patent application, publication No. WO 2014/036726 is directed to microRNA in human milk and use thereof.

U.S. patent application, publication No. U.S. 2012093874 is directed to method for screening for diet providing production of milk having immunoregulatory action.

International patent application, publication No. WO 2014/134132 is directed to milk-derived microvesicle compositions and related methods.

U.S. patent application, publication No. U.S.2013273544 is directed to methods and compositions for exosome isolation.

Melnik B. C. et.al. (2014) disclose milk as an exosomal microRNA transmitter promoting thymic regulatory T cell maturation preventing the development of atopy (Journal of Translational Medicine 2014, 12:43).

Infant formulas are artificial formulas containing various nutrients designed to provide nutrition to infants and partially or completely replace breastfeeding. The infant formula may include vegetative components and/or animal components. However, infant formulas are not identical to natural milk and they lack many components found in milk produced by mammary gland.

There is still a need in the art for improved milk formulas that will include additional beneficial nutrients from natural source. More particularly, there is a need in the art for improved milk formulas by including microvesicles of natural source, derived from various milk fractions, whereby the microvesicles include or encapsulate beneficial constituents, currently lacking from such milk formulas.

SUMMARY OF THE INVENTION

According to some embodiments, there are provided microvesicles (including such microvesicles as, exosomes (derived from milk skim fraction) and/or fat vesicles (globules) derived from milk fat fraction (layer)), which comprise or enclose, among other, various miRNA molecules. Further provided are methods of making such microvesicles and uses thereof for supplementation of various milk formulas, which do not include such natural microvesicles of animal source.

The present invention stems, in part, from the surprising finding that various microvesicles, including exosomes derived or obtained from skim fraction of milk and/or vesicles derived or obtained from fat fraction of milk, comprise various active miRNA molecules, which can be successfully conveyed to target cells (for example, normal or cancer cells) and exert a biological effect in the target cells, while maintaining a beneficial level of expression of the miRNA in the cells. In some embodiments, the present invention further stems, in part, from the surprising finding that the levels of miRNAs which are detected in high level in milk are very low in the skim fraction of infant formula and undetectable in the fat fraction of the infant formula.

In some embodiments, and without wishing to be bound to any theory or mechanisms, the beneficial effect of the microvesicles and/or the components included therein may be on a wide range of conditions and diseases and may be preventive and/or therapeutic. In some embodiments, the microvesicles and/or the components included therein (such as, miRNAs) can be protective (i.e., preventative) and/or therapeutic against such conditions as, but not limited to: infections, inflammations, cancer, and the like.

According to some embodiments, by utilizing Next Generation Sequencing (NGS) and real time PCR (RT-PCR) analysis the miRNA expression profile of skim and/or fat fraction of human, goat, bovine milk and/or infant formulas is determined. As disclosed and exemplified herein, human and mammalian milk were found to contain beneficial miRNA in microvesicles, including exosomes (from skim fraction) and fat globules in the fat layer. These miRNAs were shown to be highly conserved in human, cow and goat milk. Further, as demonstrated and exemplified herein, miRNAs present in milk exosomes and in the fat milk fraction can enter normal and tumor cells and affect their biological functions. In some exemplary embodiments, following incubation of milk derived human miRNA with normal and cancer cells, the expression of miRNA-148a was shown to be upregulated and the expression of the DNA methyltransferasel (DNMT1) target gene of miRNA-148a was down-regulated in these cells, demonstrating the potential therapeutic effect of such milk derived microvesicles and the importance of including such microvesicles in milk formulas that lack such milk-derived microvesicles of natural source.

According to some embodiments, as demonstrate herein below, highly expressed miRNAs in the fat layer of the milk are also the highly expressed in the skim fraction of milk Nevertheless, in contrast to skim milk where miRNAs are protected from degradation by exosomes, the miRNAs in the fat layer are protected and transported into fat globules. In some embodiments, miRNAs in milk are associated with RNA-binding proteins such as Agronaute-2 that protect them from degradation.

According to some embodiments, there is provided a method of obtaining microvesicles from natural milk, and uses thereof for supplementing milk formulas, such that the supplemented milk formulas comprise microvesicles of natural source, including at least some of the natural components comprised within the microvesicles.

In some embodiments, the microvesicles may include exosomes and/or other vesicles/globules derived or obtained or isolated from milk. In some embodiments, the microvesicles may include exosomes derived/obtained/isolated from skim fraction of milk. In some embodiments, the microvesicles may include exosomes derived/obtained/isolated from skim milk. In some embodiments, the microvesicles may include fat vesicles/fat globules which are derived/obtained/isolated from fat fraction of milk.

In some embodiments, the milk may be obtained from various sources, including but not limited to: bovine, goat, human, and the like. In some embodiments, the milk may be obtained at various time points before, during and/or after lactation.

In some embodiments, the microvesicles may include or encapsulate various components, such as, nucleic acids, lipids, proteins, peptides, and the like. In some embodiments, the nucleic acids may include miRNA molecules. In some embodiments, the miRNA may be selected from any of the miRNAs shown in FIGS. 1-3. In some embodiments, the miRNA may be selected from any of the miRNAs listed in Table 1 hereinbelow. In some exemplary embodiments, the miRNA molecules may include such miRNA as, but not limited to: miR-148a-3p.

In some embodiments, there is provided a milk formula composition which includes microvesicles isolated from natural milk. In some embodiments, the microvesicles are exosomes obtained from the skim milk fraction/skim fraction. In some embodiments, the microvesicles are fat vesicles/fat globules/isolated from the fat fraction of milk.

In some embodiments, the milk formula does not comprise miRNA molecules other than miRNA molecules comprised within the microvesicles derived from the natural milk.

In some embodiments, the milk formula is for use by infants.

In some embodiments, the natural milk is pasteurized. In some embodiments, the natural milk is not pasteurized.

According to some embodiments, the microvesicles are in hydrated or lyophilized form.

In some embodiments, the milk formulas do not include microvesicles of natural origin, prior to addition of the milk microvesicles of the invention. In some embodiments, the milk formulas do not include fat of animal origin, prior to addition of the milk microvesicles (such as fat globules) of the present invention.

In some embodiments, there is provided a method of enriching a milk formula, the method comprising adding an effective amount of microvesicles isolated from natural milk. In some embodiments, the microvesicles comprise miRNA molecules. In some embodiments, the microvesicles may be isolated from fat fraction and/or skim fraction of natural milk.

According to some embodiments, there is provided a method of treating cancer in a subject in need thereof, the method comprising administering a milk formula composition which includes microvesicles isolated from natural milk. In some embodiments, the administration is oral administration.

According to some embodiments, there is provided a composition for use in treating or preventing cancer in a subject in need thereof, the composition comprising milk formulation comprising microvesicles isolated from milk.

Other objects, features and advantages of the present invention will become clear from the following description and drawings.

BRIEF DESCRIPTION OF THE DRAWINGS

FIGS. 1A-E—MicroRNA expressed in cow and goat milk. FIG. 1A—MicroRNA expressed in cow milk compared to goat milk MicroRNA expression was performed by next sequencing generation in RNA isolated from cow and goat milk Venn diagram depicting miRNAs expressed in cow-goat milk. FIGS. 1B-1C—Comparison of miRNA expressed in the fat layer of the milk compared to the skim milk of pasteurized (P) and not pasteurized (NP) goat and cow milk. MicroRNA expression was performed by next sequencing generation in RNA isolated from skim and fat fraction of cow and goat milk. Venn diagram depicting miRNAs expressed in fat and skim layer of goat (FIG. 1B) and cow milk (FIG. 1C). FIGS. 1D-1E—Comparison of miRNA expressed in the skim and fat layer of pasteurized (P) compared to not-pasteurized (NP) cow and goat milk. MicroRNA expression was performed by next sequencing generation in RNA isolated from skim and fat fraction of cow and goat milk. Venn diagram depicting miRNAs expressed in fat and skim layer of pasteurized and not-pasteurized cow milk (FIG. 1D) and goat milk (FIG. 1E).

FIGS. 2A-D—Highly expressed miRNA in cow and goat milk Tables showing the ten most highly expressed miRNAs in cow and goat milk. MicroRNA expression was determined by next sequencing generation in RNA isolated from skim (whey) and fat fraction of not pasteurized (NP) and pasteurized (P) cow milk (FIGS. 2A-2B) and goat milk (FIGS. 2C-2D). Abundance profile of miRNA was shown by percentage (%) of each miRNA, from the total miRNA reads.

FIGS. 3A-D—Expression of miRNA in human milk compared to other mammalian milk. MicroRNA expression was performed by next sequencing generation in RNA isolated from human cow and goat milk. Venn diagram depicting miRNAs expressed in human-cow milk (FIG. 3A), and human-goat milk (FIG. 3B). Comparison of miRNA expressed in the fat and skim layers of the human milk. MicroRNA expression was performed by next sequencing generation in RNA isolated from skim and fat fraction of human milk Venn diagram depicting miRNAs expressed in fat and skim layers of human milk (FIG. 3C). The ten highly expressed miRNA in human milk. Abundance profile of miRNA was shown by percentage (%) of each miRNA, from the total miRNA reads by NGS (FIG. 3D).

FIG. 4C—The expression of miRNA-148a in the skim and fat fraction of the milk of 16 different mothers at one month of lactation was analyzed by qRT-PCR. The qRT-PCR results were calculated by Delta-Delta CT Method (ΔΔCt) and normalized against RNU6B. The ΔΔCt value of miRNA-148a in each fraction is shown by box-and-whisker plot (FIG. 4C)

FIGS. 8A-D. MicroRNA uptake by different type of cells. Labeled milk exosomes and the fat layer isolated from human milk were incubated with normal intestinal cells (CRL 1831), colon cancer cells (Lim 1215) or leukemia cells (K562). Images shown in FIGS. 8A and 8C were obtained by fluorescent microscope analysis after 2 hours incubation with labeled milk exosomes (FIG. 8A) and fat layer vesicles (FIG. 8C). Expression of miRNA-148a in the different cells incubated with (Exo+) or without (CONT) exosomes was analyzed by qRT-PCR. The bar graphs shown in FIG. 8B represent these results. FIG. 8D—Bar graphs showing the expression of miRNA-148a in CRL 1831 incubated with exosomes (+EXO), lipid fraction or without (CONT) as determined by qRT-PCR analysis. The qRT-PCR results were calculated by Delta-Delta CT method ($\Delta\Delta$Ct), values were normalized against RNU6B.

FIGS. 9A-9D. Expression of DNMT1 in cells incubated with the fat layer and exosomes isolated from human milk. Exosomes isolated from human milk were incubated with normal colon cells (CRL1831). Expression of miRNA-148a in cells incubated with (EXO+) or without (CONT) exosomes was analyzed by qRT-PCR. The qRT-PCR results were calculated by Delta-Delta CT Method ($\Delta\Delta$Ct), values were normalized against RNU6B (FIG. 9A). Expression of DNMT1 in cells described in (FIG. 9B) was analyzed by qRT-PCR. The qRT-PCR results were calculated by Delta-Delta CT Method ($\Delta\Delta$Ct), values were normalized against beta actin. The fat layer of human milk was incubated with K562 leukemia cells. Expression of miRNA-148a with (FAT) or without (CONT) fat was analyzed by qRT-PCR. The qRT-PCR results were calculated by Delta-Delta CT Method ($\Delta\Delta$Ct), values were normalized against RNU6B (C). Expression of DNMT1 in cells described in (FIG. 9C) was analyzed by qRT-PCR. The qRT-PCR results were calculated by Delta-Delta CT Method ($\Delta\Delta$Ct), values were normalized against beta actin (FIG. 9D).

FIG. 10A—Pictograms showing mouse intestine sections incubated with Labeled milk exosomes isolated from breast milk and labeled fat fraction from breast milk. Images were obtained by fluorescent microscope analysis after 24 hours of incubation;

FIG. 10B—Bar graphs showing expression of miRNA-148a in intestine with (Exo+) or lipid fraction exosomes as determined by qRT-PCR. The qRT-PCR results were calculated by Delta-Delta CT Method ($\Delta\Delta$Ct), values were normalized against RNU6B.

DETAILED DESCRIPTION

Figure 4A:
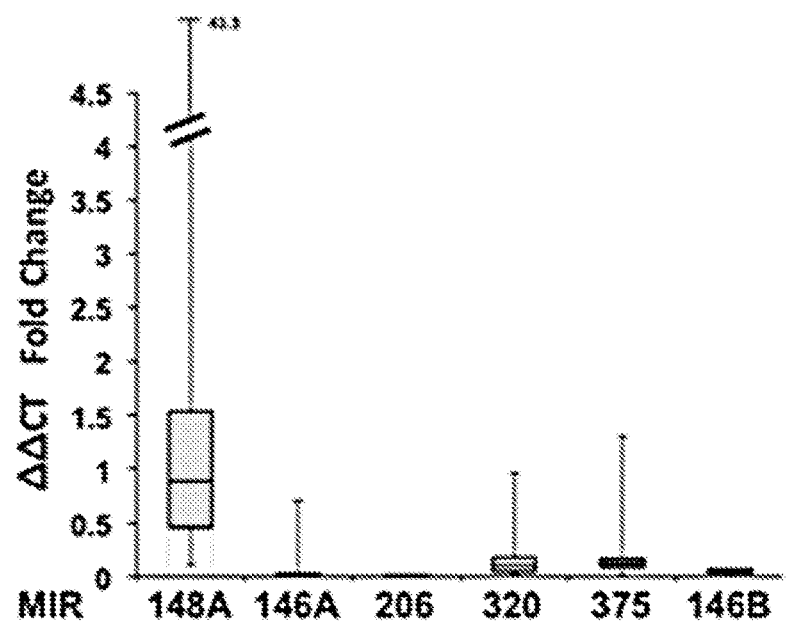
FIGS. 4A-C—Expression of selected miRNAs in human milk. Total RNA from the skim and fat fraction of the milk obtained from 16 different mothers at one month of lactation was isolated. Expression of miRNA-148a, miRNA-146a miRNA-146b, miRNA-206, miRNA-375 and miRNA-320 were analyzed by qRT-PCR. The qRT-PCR results were calculated by Delta-Delta CT Method (ΔΔCt) and normalized against RNU6B. The ΔΔCt values of miRNA in the fat fraction (FIG. 4A) and skim milk (FIG. 4B) are shown by box-and-whisker plots.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

The following are terms which are used throughout the description and which should be understood in accordance with the various embodiments to mean as follows:

The terms "milk" and "natural milk" may interchangeably be used and are directed to include the nourishing liquid produced by the mammary glands of mature female mammals including, but not limited to, after giving birth to provide nourishment for their young. The milk may be divided into two major fractions: a liquid fraction, termed herein "skim" (or "skim milk" or "skim fraction", or "skim milk fraction") and a "fat" fraction. The skim milk fraction is a milk fraction, obtained after removal of milk fat. In some embodiments, the terms "whey", "whey fraction", "skim milk", "skim fraction" and "skim milk fraction" may interchangeably be used. In some embodiments, the skim fraction includes the whey fraction.

The term "treatment" as used herein refers to both therapeutic treatment and prophylactic or preventative measures.

The term "microvesicle" refers to a natural lipid particle vesicle be formed by a various cellular, including budding from the cytoplasmic membrane, release of apoptotic bodies, and/or exocytosis. The term microvesicles as used herein is directed to natural vesicles (typically in the size of 20-1000 nm in diameter) which are derived, obtained and/or isolated from milk. As used herein, the microvesicles may include various types of vesicles, such as, exosome, fat vesicles and the like, each may be obtained from different fraction of the milk, and each may be differentiated based on size, lipid composition and components included therewith.

The term "exosome" refers to a type of microvesicle, with a diameter of between 30 and 100 nm. Exosomes are either released from the cell when multivesicular bodies fuse with the plasma membrane or are released directly from the plasma membrane. An exosome, as used herein is obtained, derived and/or isolated from the skim fraction of milk and in some embodiments, more particularly from the skim milk fraction.

The terms "microRNA" and "miRNA" are directed to a small non-coding RNA molecule that can function in transcriptional and post-transcriptional regulation of target gene expression.

The term "milk formula" (also referred to herein as "infant formula") is directed to a nutritional composition, which is designed to contain sufficient nutritional components (such as, protein, carbohydrate, fat, vitamins, and minerals) to serve as nutrition source when provided in sufficient quantity. In some embodiments, the milk formula is also referred to as infant formula, as it is designed for use by infants. In some embodiments, the milk formula is artificial. In some embodiments, the milk formula may include components of vegetative origin, animal origin or combinations thereof. In some embodiments, the milk formula does not include components derived from the fat fraction of milk. In some embodiments, the milk formula does not include miRNA molecules, other than miRNAs encapsulated within microvesicles obtained or isolated form natural milk source.

The term "composition" as used herein refer to a composition which include milk derived microvesicles, and one or more ingredients, such as, a milk-formula. In some embodiments, the composition is a milk formula comprising milk-derived microvesicles. In some embodiments, the composition is a therapeutic composition.

According to some embodiments, there are provided microvesicles obtained from natural milk, which comprise various miRNA molecules, and uses thereof for supplementation of various milk formulas, lacking otherwise such natural microvesicles of animal source. In some embodiments, there are provided compositions of milk formula which comprise the milk derived microvesicles of the invention. In some embodiments, there are provide compositions comprising milk formula and milk derived microvesicles.

There is provided herein according to some embodiments, a method of obtaining microvesicles from milk, the method include fractionating the milk and obtaining a skim fraction and a fat fraction. The method further include a step of isolating/obtaining exosomes from the skim fraction and/or obtaining/isolating vesicles from the fat fraction of the milk. In some embodiments, milk is fractionated by centrifugation at 5000 g for 30 minutes at 4° C. Three fractions may be obtained from the milk: lipids, skim milk and cells. The skim fraction is centrifuged at 12000 g for 1 hour at 4° C. Next, the supernatant may be filtered through filters (for example, 5 and 0.45 μm filters). Exosomes are pelleted, for example, by incubation with reagents, such as, Exoquick (SBI , EXOQ20A-1).

In some embodiments, there is provided a method for obtaining microvesicles from milk, the method comprising centrifugation an initial volume of milk at 1000-8000 g (for example, 4000 g) for 1-3 hours (for example, 1 hour) at 4° C., to obtain two layers of milk: fat and skim milk. The skim layer may then be centrifuged at 8000-15000 g (for example, at 10000 g) for 15-120 minutes (for example, for 30 minutes) at 4° C. At this point, the pellet may be discarded and the supernatant (Sup) may be used in the next steps. The Sup may be ultra-centrifuged for any number of times, for example, twice, at 80000-150000 g (for example at 100000 g), for 30-180 minutes (for example, 70 minutes) at 4° C. The resulting pellet includes microvesicles (such as exosomes), which contain miRNA molecules. Likewise, the fat globules in the fat layer contain miRNA molecules. In some embodiments, the microvesicles obtained by this method are advantageous as they are safe for further use. The preparation and manipulation only involves centrifugation steps in the presence of a suitable buffer (such as, PBS) which is used as a washing reagent and does not involve other reagents or devices that may render the process expensive and less safe. In some embodiments, the microvesicles obtained by this method can be readily added to milk formulas, to supplement these milk formulas. Further, as exemplified herein below, such microvesicles contain miRNAs which are stable and active, and can further provide a preventative and/or therapeutic effect when added to milk formulas.

In some embodiments, the microvesicles may include exosomes and/or other vesicles derived or obtained or isolated from milk. In some embodiments, the microvesicles may include exosomes derived/obtained/isolated from skim fraction of milk. In some embodiments, the microvesicles may include exosomes derived/obtained/isolated from skim milk. In some embodiments, the microvesicles may include vesicles derived/obtained/isolated from fat fraction of milk.

In some embodiments, the milk may be obtained from various suitable sources, including but not limited to: bovine (cow), goat, human, and the like. In some embodiments, the milk may be obtained at various time points before, during and/or after lactation. The milk may be obtained at various time points during the day (for example, morning, evening, midnight). The milk may be obtained at various after birth.

According to some embodiments and as further exemplified herein, the microvesicles disclosed herein include or encapsulate various biological components, including, various miRNA molecules, at different abundancy, proteins, lipids, metabolites and the like.

In some embodiments, the microvesicles disclosed herein may be isolated from milk of various origin at various time points and the composition of the microvesicles, and the components included therein may be identical or different between the milk origin and/or time points.

According to some embodiments, the microvesicles may be obtained from bovine (cow) milk, before or after pasteurization. The microvesicles may be obtained from skim fraction and/or fat fraction of the cow milk.

According to some embodiments, the microvesicles may be obtained from goat milk, before or after pasteurization. The microvesicles may be obtained from skim fraction and/or fat fraction of the goat milk.

According to some embodiments, the microvesicles may be obtained from human female breast milk. The microvesicles may be obtained from skim fraction and/or fat fraction of the human milk. In some embodiments, the human milk may be obtained from breast milk of a term baby mother and/or from the breast milk of a pre-term baby mother.

In some embodiments, the microvesicles obtained from milk may be analyzed to identify components carried/included/encapsulated therewith.

In some embodiments, the microvesicles obtained may contain various molecules, including, but not limited to: nucleic acid molecules, proteins, peptides, lipids, minerals, and the like.

In some embodiments, the microvesicles include/encapsulate/comprise one or more miRNA molecules. In some embodiments, the miRNA molecules may be one or more of the miRNAs selected from the group consisting of: miR-6073, miR-148a-3p, miR-320-3p, miR-378-3p, miR-146b-5p, miR-22-3p, miR-99a-5p, let-7b-5p, miR-30a-5p, miR-184, miR-146a-5p, miR-22-3p, miR-423-5p, miR-30d, miR-1246, miR-6131, miR-3182, miR-1, miR-200a, let-7a-5p, miR-7-5p, miR-99b-5p, miR-181a, miR-151-3p, miR-4448, miR-3135b, miR-99a-5p, miR-92b, miR-375, miR-21-5p, miR-200c, miR-7704, miR-191-5p, miR-200b, miR-24-3p, miR-205, miR-4488, miR-423-3p, miR-26a-5p, miR-22-3p, miR-9-5p, miR-143-3p, miR-27b-3p, miR-25-3p, miR-193b-3p, let-7i-5p, miR-7641, miR-361-3p, miR-4497, miR-186-5p, let-7c-5p, miR-193a-5p, miR-100, miR-24-3p, miR-125b, miR-148a-5p, let-7g-5p, miR-4443, miR-27a-3p, miR-1839, miR-140-3p, miR-191, let-7f-5p, miR-29a-3p, miR-30c-5p, miR-33a-5p, miR-23b-3p, miR-652, miR-200a, miR-100-5p, miR-141, miR-190b, miR-224-5p, miR-181b-5p, miR-532-5p, miR-23a, miR-148b-3p, miR-28-3p, miR-140, miR-210, miR-30e-5p, miR-4532, miR-378c, miR-320b, miR-6510-3p, miR-125b-3p, miR-125b-5p, miR-221-3p, miR-2340, miR-10a-5p, miR-320c, miR-369-3p, miR-30b-5p, miR-361-3p, miR-1307-3p, miR-222-3p, miR-574-3p, miR-3196, miR-200a-5p, miR-1307-5p, miR-125a-5p, miR-4516, miR-423-3p, miR-182, miR-345-5p, miR-629-5p, miR-122, miR-133a-3p, miR-425-5p, miR-19b-3p, let-7d-3p, miR-4492, miR-452-5p, let-7d-5p, miR-93-5p, miR-106b-3p, miR-378i, miR-125a, miR-668-3p, miR-101-3p, miR-378c, miR-185, miR-30a-3p, miR-16-5p, miR-3656, miR-142-5p, miR-101, miR-192-5p, miR-223-3p, miR-146a, miR-4508, miR-103-3p, miR-29a, miR-151-5p, miR-429, miR-320d, miR-99b-3p, let-7i-3p, miR-378d, miR-183, miR-23b-3p, miR-146b-3p, miR-3615, miR-107-3p, miR-182, miR-22-5p, miR-335, miR-203a-3p, miR-21-3p, miR-378d, miR-589-5p, miR-6869-5p, miR-2110, miR-26b-5p, miR-181a-2-3p, miR-664a-5p, miR-192, miR-452, miR-21-5p, miR-193a-3p, miR-425-3p, miR-339-3p, miR-125a-3p, miR-941, let-7b-3p, miR-106b-3p, miR-152, miR-224, let-7e-5p, miR-378e, miR-484, miR-502a, miR-128-3p, miR-17-5p, miR-197-3p, miR-378-5p, miR-28-5p, miR-132, miR-223-5p, miR-339b, let-7d-3p, miR-27a-5p, miR-30e-3p, miR-27a-3p, miR-542-3p, miR-23a, miR-660-5p, miR-361-5p, miR-378g, miR-324-3p, miR-1307-5p, miR-30a-3p, miR-934, miR-16b, miR-4330, miR-181a-3p, miR-24-2-5p, miR-365-3p, miR-500-3p, miR-206, miR-155-5p, miR-328-3p, miR-4286, miR-494, miR-30c-2-3p, miR-16b-5p, miR-744, miR-150, miR-6724-5p, miR-5787, miR-20a-5p, miR-29c, miR-335-5p, miR-99b-3p, miR-339-5p, miR-29c-5p, miR-335-3p, miR-2904, miR-28, miR-2478, miR-760-3p, miR-147, miR-183, miR-885, miR-30e-3p, miR-15b-5p, miR-200b-5p, miR-223-5p, miR-532-3p, miR-7977, miR-194, miR-339a, miR-374b-5p, miR-671-5p, miR-378f, miR-10a, miR-145-5p, miR-660, miR-181b, miR-124a, miR-28-3p, miR-135a, miR-499-5p, miR-29b, miR-421-3p, miR-365b-5p, miR-5100, miR-98-5p, miR-221-3p, miR-106b-5p, miR-25-5p, miR-1261, miR-4302, miR-16a, miR-326-3p, miR-92b, miR-338-5p, miR-671-3p, miR-34a, miR-30b-3p, miR-342-3p, miR-92a-1-5p, miR-22-5p, miR-199c-3p, miR-196a, miR-6832-3p, miR-16a-5p, miR-30f-5p, miR-30f, miR-4791, miR-19a, miR-363-3p, miR-15a-5p, miR-500a-3p, miR-2285aa, miR-150, miR-148b-5p, miR-196a, miR-486, miR-30d-5p, miR-2284x, miR-2285t, miR-3431-5p, miR-2284y, miR-340-5p, miR-6529a, miR-4693-3p, miR-379-5p, miR-345-3p, miR-7154-3p, miR-140-5p, miR-3432-5p, miR-411a, miR-429, miR-3431-3p, miR-142-3p, miR-3432a, miR-142-5p, miR-429, miR-718, miR-382-5p, miR-769, miR-381, let-7a-3p, miR-493-5p, miR-362-5p, miR-342, miR-885-3p, miR-493-3p, miR-374a-3p, miR-146b-3p, miR-1777b, miR-409-3p, miR-7113-5p, miR-374a, miR-2419-5p, miR-3958-3p, miR-2285f, miR-345-5p, miR-136-3p, miR-1468-5p, miR-1273g-3p, miR-30f-, 3p, let-7f-3p, miR-708-3p, miR-380-3p, miR-1271, miR-664b, miR-1469, miR-2284ab, miR-1343, miR-20b, miR-340-3p, miR-2285ae, miR-96, miR-2463, miR-411a-5p, miR-204-5p, miR-500-5p, miR-2885, miR-29b-3p, miR-125a-5p, miR-32, miR-32-5p, miR-451, miR-106a-5p, miR-323b, miR-6741-5p, miR-6119-5p, miR-126-3p, miR-374a-5p, miR-15b-3p, miR-136-3p, miR-146a, miR-323a-3p, miR-376c-3p, miR-410-3p, miR-331-3p, miR-370, miR-2387, miR-708-5p, miR-655, miR-2285k, miR-2284j, miR-1296, miR-6120-3p, miR-4454, let-7b-3p, miR-127, miR-2285ad, miR-6524, miR-2285p, miR-3976, miR-l10b-5p, miR-107, miR-215, miR-432-5p, miR-2887, miR-762, miR-139, miR-1388-5p, miR-1271-5p, miR-2285x, miR-3178, miR-2285e, miR-3959-5p, miR-2419-3p, miR-7-1-3p, miR-330, miR-340, miR-323, miR-296-3p, miR-324-5p, miR-485, miR-1249-5p, miR-2285b, miR-141-5p, miR-532-3p, let-7f-2-3p, miR-7862, miR-6517, miR-495-3p, miR-99a-3p, miR-215-5p, miR-299-3p, miR-6729-5p, miR-204-3p, miR-2890, miR-409-3p, miR-505-3p, miR-2484, miR-342-5p, miR-6522, miR-2336, miR-519d-5p, miR-1291, miR-411a-5p, miR-382-3p, miR-221-5p, miR-9-3p, miR-487b-3p, miR-502b-5p and miR-369-5p. Each possibility is a separate embodiment.

In some embodiments, the microvesicles include/encapsulate miRNA molecules, the miRNA molecules comprises one or more of: miR-6073, miR-148a-3p, miR-320-3p, miR-378-3p, miR-146b-5p, miR-22-3p, miR-99a-5p, let-7b-5p, miR-30a-5p, miR-184, miR-146a-5p, miR-22-3p, miR-423-5p, miR-30d, miR-1246, miR-6131, miR-3182, miR-1, miR-200a, let-7a-5p, miR-7-5p, miR-99b-5p, miR-181a, miR-151-3p, miR-4448, miR-3135b, miR-99a-5p, miR-92b, miR-375, miR-21-5p, miR-200c, miR-7704, miR-191-5p, miR-200b, miR-24-3p, miR-205, miR-4488, miR-423-3p, miR-26a-5p, miR-22-3p, miR-9-5p, miR-143-3p, miR-27b-3p, miR-25-3p, miR-193b-3p, let-7i-5p, miR-7641, miR-361-3p, miR-4497, miR-186-5p, let-7c-5p, miR-193a-5p, miR-100, miR-24-3p, miR-125b, miR-148a-5p, let-7g-5p, miR-4443, miR-27a-3p, miR-1839, miR-140-3p, miR-191, let-7f-5p, miR-29a-3p, miR-30c-5p, miR-33a-5p, miR-23b-3p, miR-652, miR-200a, miR-100-5p, miR-141, miR-190b, miR-224-5p, miR-181b-5p, miR-532-5p, miR-23a, miR-148b-3p, miR-28-3p, miR-140, miR-210, miR-30e-5p, miR-4532, miR-378c, miR-320b, miR-6510-3p, miR-125b-3p, miR-125b-5p, miR-221-3p, miR-2340, miR-10a-5p, miR-320c, miR-369-3p, miR-30b-5p, miR-361-3p, miR-1307-3p, miR-222-3p, miR-574-3p, miR-3196, miR-200a-5p, miR-1307-5p, miR-125a-5p, miR-4516, miR-423-3p, miR-182, miR-345-5p, miR-629-5p, miR-122, miR-133a-3p, miR-425-5p, miR-19b-3p, let-7d-3p, miR-4492, miR-452-5p, let-7d-5p, miR-93-5p, miR-106b-3p, miR-378i, miR-125a, miR-668-3p, miR-101-3p, miR-378c, miR-185, miR-30a-3p, miR-16-5p, miR-3656, miR-142-5p, miR-101, miR-192-5p, miR-223-3p, miR-146a, miR-4508, miR-103-3p, miR-29a, miR-151-5p, miR-429, miR-320d, miR-99b-3p, let-7i-3p, miR-378d, miR-183, miR-23b-3p, miR-146b-3p, miR-3615, miR-107-3p, miR-182, miR-22-5p, miR-335, miR-203a-3p, miR-21-3p, miR-378d, miR-589-5p, miR-6869-5p, miR-2110, miR-26b-5p, miR-181a-2-3p, miR-664a-5p, miR-192, miR-452, miR-21-5p, miR-193a-3p, miR-425-3p, miR-339-3p, miR-125a-3p, miR-941, let-7b-3p, miR-106b-3p, miR-152, miR-224, let-7e-5p, miR-378e, miR-484, miR-502a, miR-128-3p, miR-17-5p, miR-197-3p, miR-378-5p, miR-28-5p, miR-132, miR-223-5p, miR-339b, let-7d-3p, miR-27a-5p, miR-30e-3p, miR-27a-3p, miR-542-3p, miR-23a, miR-660-5p, miR-361-5p, miR-378g, miR-324-3p, miR-1307-5p, miR-30a-3p, miR-934, miR-16b, miR-4330, miR-181a-3p, miR-24-2-5p, miR-365-3p, miR-500-3p, miR-206, miR-155-5p, miR-328-3p, miR-4286, miR-494, miR-30c-2-3p, miR-16b-5p, miR-744, miR-150, miR-6724-5p, miR-5787, miR-20a-5p, miR-29c, miR-335-5p, miR-99b-3p, miR-339-5p, miR-29c-5p, miR-335-3p, miR-2904, miR-28, miR-2478, miR-760-3p, miR-147, miR-183, miR-885, miR-30e-3p, miR-15b-5p, miR-200b-5p, miR-223-5p, miR-532-3p, miR-7977, miR-194, miR-339a, miR-374b-5p, miR-671-5p, miR-378f, miR-10a, miR-145-5p, miR-660, miR-181b, miR-124a, miR-28-3p, miR-135a, miR-499-5p, miR-29b, miR-421-3p, miR-365b-5p, miR-5100, miR-98-5p, miR-221-3p, miR-106b-5p, miR-25-5p, miR-1261, miR-4302, miR-16a, miR-326-3p, miR-92b, miR-338-5p, miR-671-3p, miR-34a, miR-30b-3p, miR-342-3p, miR-92a-1-5p, miR-22-5p, miR-199c-3p, miR-196a, miR-6832-3p, miR-16a-5p, miR-30f-5p, miR-30f, miR-4791, miR-19a, miR-363-3p, miR-15a-5p, miR-500a-3p, miR-2285aa, miR-150, miR-148b-5p, miR-196a, miR-486, miR-30d-5p, miR-2284x, miR-2285t, miR-3431-5p, miR-2284y, miR-340-5p, miR-6529a, miR-4693-3p, miR-379-5p, miR-345-3p, miR-7154-3p, miR-140-5p, miR-3432-5p, miR-411a, miR-429, miR-3431-3p, miR-142-3p, miR-3432a, miR-142-5p, miR-429, miR-718, miR-382-5p, miR-769, miR-381, let-7a-3p, miR-493-5p, miR-362-5p, miR- 342, miR-885-3p, miR-493-3p, miR-374a-3p, miR-146b-3p, miR-1777b, miR-409-3p, miR-7113-5p, miR-374a, miR-2419-5p, miR-3958-3p, miR-2285f, miR-345-5p, miR-136-3p, miR-1468-5p, miR-1273g-3p, miR-30f-, 3p, let-7f-3p, miR-708-3p, miR-380-3p, miR-1271, miR-664b, miR-1469, miR-2284ab, miR-1343, miR-20b, miR-340-3p, miR-2285ae, miR-96, miR-2463, miR-411a-5p, miR-204-5p, miR-500-5p, miR-2885, miR-29b-3p, miR-125a-5p, miR-32, miR-32-5p, miR-451, miR-106a-5p, miR-323b, miR-6741-5p, miR-6119-5p, miR-126-3p, miR-374a-5p, miR-15b-3p, miR-136-3p, miR-146a, miR-323a-3p, miR-376c-3p, miR-410-3p, miR-331-3p, miR-370, miR-2387, miR-708-5p, miR-655, miR-2285k, miR-2284j, miR-1296, miR-6120-3p, miR-4454, let-7b-3p, miR-127, miR-2285ad, miR-6524, miR-2285p, miR-3976, miR-l10b-5p, miR-107, miR-215, miR-432-5p, miR-2887, miR-762, miR-139, miR-1388-5p, miR-1271-5p, miR-2285x, miR-3178, miR-2285e, miR-3959-5p, miR-2419-3p, miR-7-1-3p, miR-330, miR-340, miR-323, miR-296-3p, miR-324-5p, miR-485, miR-1249-5p, miR-2285b, miR-141-5p, miR-532-3p, let-7f-2-3p, miR-7862, miR-6517, miR-495-3p, miR-99a-3p, miR-215-5p, miR-299-3p, miR-6729-5p, miR-204-3p, miR-2890, miR-409-3p, miR-505-3p, miR-2484, miR-342-5p, miR-6522, miR-2336, miR-519d-5p, miR-1291, miR-411a-3p, miR-382-3p, miR-221-5p, miR-9-3p, miR-487b-3p, miR-502b-5p and miR-369-5p. Each possibility is a separate embodiment.

In some embodiments, the miRNA molecules may include such molecules as, but not limited to: miR-148a-3p, miR-6073, miR-220c, miR-200b; miR-99a-5p, miR-30a-5p, miR30d, miR-320-3p, miR7a-5p, miR-26a-5p, miR-21-5p, miR-92b, miR-99a-5p, miR-423-5p, miR-let-7b-5p, miR-375, miR-let-7f-5p, miR-let-7g-5p. In some embodiments, the miRNA molecules may be selected from any of the molecules listed in the Tables shown in FIG. 1, FIG. 2 and/or FIG. 3. Each possibility is a separate embodiment. In some embodiments, he miRNA molecules may be selected from any of the molecules listed in Table 1, herein below.

In some embodiments, the microvesicles comprise or encapsulate miR148a-3p.

In some embodiments, as exemplified herein, the milk derived microvesicles of the invention include highly expressed miRNAs which are conserved in different types of milk from various origin. For example miRNA-148a is conserved in mammalians throughout evolution as are other highly expressed miRNAs in milk such as mir-320, 375, 99 which are also conserved in different species.

According to some embodiments, as exemplified herein similar miRNA expression profile is identified in the skim and fat layers of pasteurized and unpasteurized cow and goat milk According to some embodiments, pasteurizing milk does not affect (destroy) miRNA, in particular miRNA contained within the microvesicles of the present invention.

According to some embodiments, as exemplified herein, the miRNA content in various infant-milk formulas is significantly lower than that found in cow, goat, or human milk and in most cases is absent.

According to some embodiments, and without wishing to be bound by any theory or mechanism, the transfer/encapsulation of milk-derived miRNAs in exosomes and other vesicles may aid miRNAs survive in the gastrointestinal tract, and their subsequent uptake into the intestine and transfer to the bloodstream.

According to some embodiments, and as exemplified herein, human, cow and/or goat miRNAs present in the fat milk fraction are active as they are able to enter cells and further affect their biological function. In some embodiments, miRNAs present in either the exosomes or the fat layer of milk can enter normal and tumor cells and have the ability to regulate cellular biological functions.

In some embodiments, microvesicles derived from milk which comprise miR-148 can be used to downregulate expression of DNMT1 in normal and/or cancer cells.

In some embodiments, the composition/identity of the miRNA molecules may be identical or different between microvesicles obtained from milk of different origin. In some embodiments, the relative abundancy of the miRNA molecules may be identical or different between microvesicles obtained from milk of different origin. In some embodiments, the composition/identity or relative abundancy of the miRNAs may be identical or different between microvesicles isolated from milk obtained from different times of the day.

According to some embodiments, there is provided a use of microvesicles derived/isolated from milk for supplementing milk formulas, such that the supplemented milk formulas comprise microvesicles of natural source, including the natural components comprised within the microvesicles.

According to some embodiments, there is provided a milk formula comprising a microvesicle obtained or isolated from milk. According to some embodiments, there is provided a composition comprising milk formula comprising a microvesicle obtained or isolated from milk.

In some embodiments, the milk formulas do not include microvesicles of natural origin, other than the added milk microvesicles of the present invention. In some embodiments, the milk formulas do not include fat of animal origin other than the added microvesicles (fat globules) of the present invention.

In some embodiments, the microvesicles may be added to the milk formula in any appropriate form. In some embodiments, the microvesicles may be added to the milk formula in the presence of a carrier. In some exemplary embodiments, the microvesicles may be added to the milk formula in a buffer, such as, for example, PBS, TBS. and the like. In some embodiments, the microvesicles may be added to the milk formula in a dehydrated form. In some embodiments, the microvesicles may be added to the milk formula in a lyophilized form. In some embodiments, the composition of milk formula and microvesicles may be in liquid or hydrated form. In some embodiments, the composition of milk formula and microvesicles is intended for oral use.

In some embodiments, the microvesicles added to the formula preserve at least part of the biological activity and/or chemical stability of the components included therewith.

In some embodiments, by adding microvesicles derived from milk to the milk formula, the such generated/obtained milk formula composition may be able to exert a preventative and/or therapeutic effect. In some embodiments, the preventative and/or therapeutic effect may not be obtained by a milk formula which does not include the microvesicles isolated from milk In some embodiments, the protective effect of the microvesicles is against a vast range of conditions. In some embodiments, the conditions are infection, inflammation, cancer, and the like.

According to some embodiments, and without wishing to be bound to any theory or mechanism, by including the milk derived microvesicles in milk formulas composition, the milk formulas are improved and they are able to supply nutritional needs and contribute to infant health leading to adequate growth of the brain, the immune system development and for preventing childhood infection diseases.

According to some embodiments, the protective effect of the microvesicles is against any type of cancer. In some embodiments, the cancer is leukemia.

According to some embodiments, there is provided a method of treating or preventing a condition, such as cancer, by providing microvesicles isolated from milk to the subject. In some embodiments, the subject is an infant. In some embodiments, the microvesicles are provided in a milk formula composition.

According to some embodiments, there is provided a use of microvesicles isolated from milk for the treatment or prevention of cancer in a subject in need thereof. In some embodiments, the subject is an infant. In some embodiments, the microvesicles are administered orally, in a cmoposition which includes milk formula.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1

Expression Profile of miRNA in Human Breast Milk, Bovine and Goat Milk

Analysis of the profile expression of miRNA in human breast milk, bovine and goat milk was performed by next generation sequencing (NGS): Milk samples were collected from human female mothers from pre-term and term babies at different time points after delivery. Preterm mothers were mothers to babies born at weeks 28-36 of pregnancy. Term mothers were mothers to babies born at weeks 37-42 to pregnancy. Milk samples were collected on 2 days postpartum-colostrum, 1 month postpartum, 3 month postpartum, 6 month postpartum and 9 months postpartum. Likewise, milk samples and from cow and goat milk were collected before and after pasteurization. Fat and skim fractions of the milk were separated by several centrifugations. Milk is fractionated by centrifugation at 5000 g for 30 minutes at 4° C. Three fractions are obtained from the milk: lipids, skim milk and cells.

NGS was used to analyze the profile of miRNA expression in the various milk samples. Total RNA isolation from samples was performed with the miRNeasy mini kit (Qiagen) following lysis and homogenization in TrIzol, and a barcoded small RNA cDNA library was prepared from two layers of milk Expression of miRNA in cow and goat milk. NGS was used to determine the expression profiles of miRNA in the fat and skim fraction of bovine and goat milk, before and after pasteurization Small RNAs including mature miRNA were sequenced in the fat and skim fractions of the milk samples using Ilumina small RNA next sequencing generation. The NGS results indicated a high similarity between the miRNA expressed in human, cow and goat milks: 97% of the miRNAs expressed in cow milk were also expressed in goat milk and 94% of the miRNAs expressed in goat milk were also expressed in cow milk (FIG. 1A). The miRNA expressed in the fat and skim layers of pasteurized and non-pasteurized cow and goat milk were similar (FIG. 1B and 1C). Furthermore, the results indicate that pasteurization did not affect the profile expression of miRNA in cow or goat milk, as shown in FIGS. 1D and 1E.

Analyses of the identity of the miRNAs show that the ten most highly expressed miRNA were found in the different layers of both the cow and goat milk (FIGS. 2A-D). For example, miRNA 148a -3p was highly expressed in the miRNA in the fat and skim fractions of both goat and cow milk before and after pasteurization.

Figure 4B:
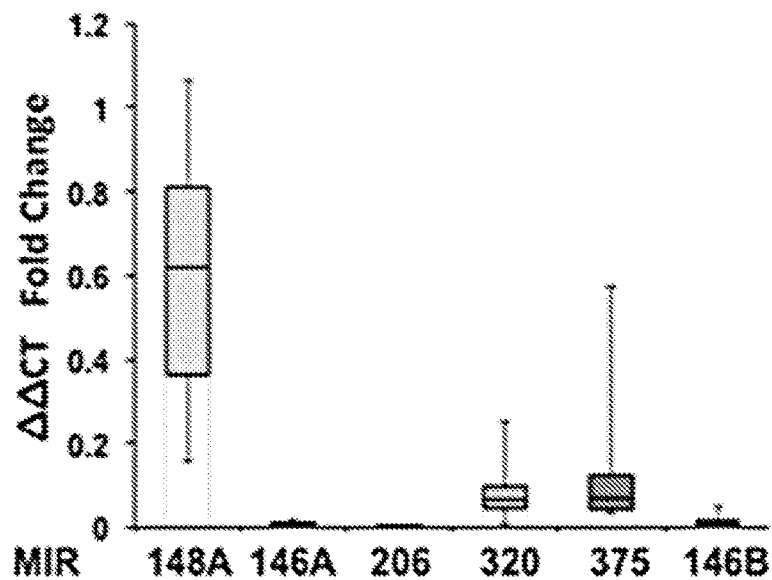
Figure 4C:
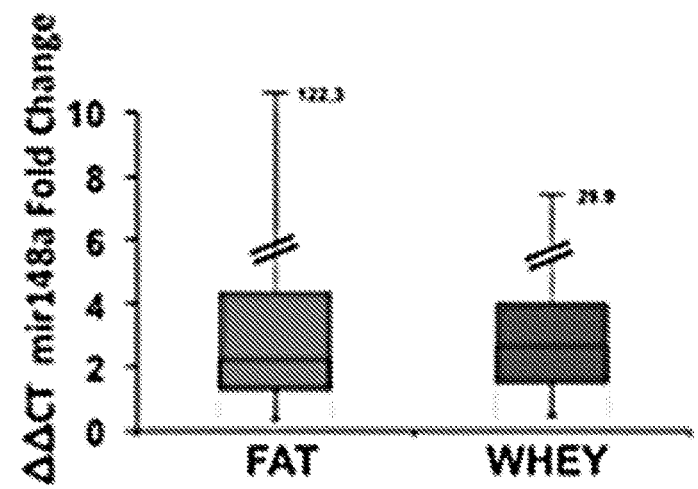
Figure 5A:
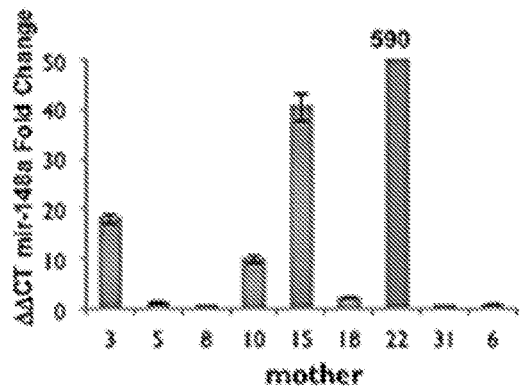
FIGS. 5A-D—Graphs showing the expression of the miRNA-148a in the skim and fat fraction of breast milk. Total RNA from the skim and fat fraction of the colostrum (FIGS. 5A-5B, respectively) and the skim and fat fraction from milk of different mothers at one month of lactation (FIGS. 5C-5D) was isolated and expression of miRNA-148a was analyzed by qRT-PCR. The qRT-PCR results were calculated by Delta-Delta CT Method (ΔΔCt), values were normalized against RNU6B.
Figure 5B:
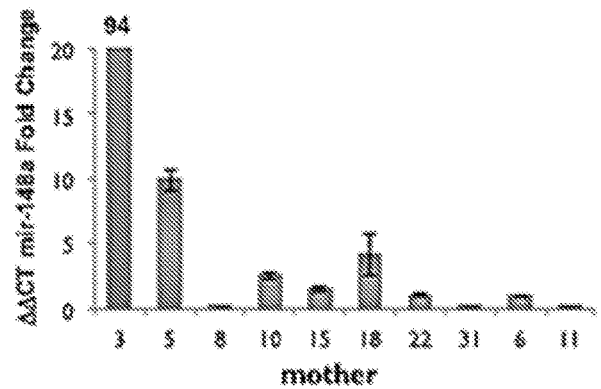
Figure 5C:
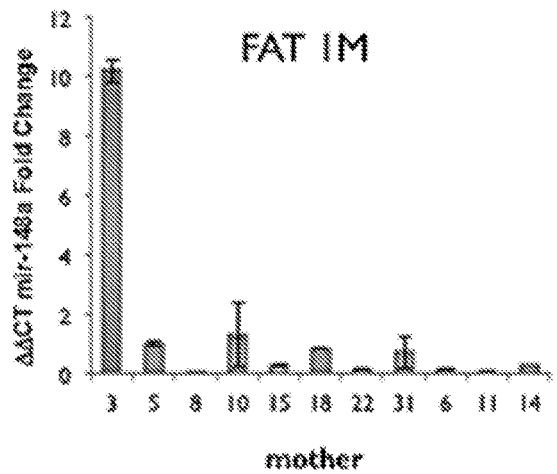
Figure 5D:
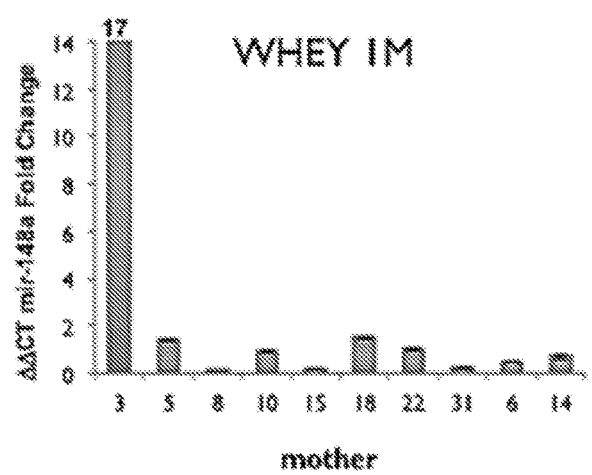

A comparison of miRNA expression in human and other mammalian milks indicated that 95% of the miRNA expressed in human milk was also expressed in cow and goat milk, 95% of the miRNA expressed in cow milk was also expressed in human milk and 83% of the miRNA expressed in goat milk was also expressed in human milk (FIG. 3A and 3B). In all the types of milk analyzed, miRNA expression in the fat and skim layers of human milk were similar (FIG. 3C). Moreover, the most highly expressed miRNA were similar in the human, cow and goat fractions of the milk (FIGS. 2A-D and 3D). miRNA 148a-3p, one of the most highly expressed miRNAs in the fat and skim layers of goat and cow milk before and after pasteurization was also highly expressed in breast milk (FIG. 3D). The expression of miRNA 148a-3p in the skim and fat layers of milk of 20 mothers indicates that this miRNA was highly expressed in both layers, compared to other milk miRNAs (FIG. 4A and 4B). The expression of miRNA 148a-3p was similar in the two layers of the milk (FIG. 4C). miRNAs 148a-3p is generally considered to have been conserved throughout evolution as are other highly expressed miRNAs in milk.

The expression levels of all the detected miRNAs in the fat and skim fractions of cow milk (pasteurized or not pasteurized), goat milk (pasteurized or not pasteurized) and human milk are listed in Table 1, below. As detailed above, NGS was performed in the fat and skim layers of cow, goat and human milk. In cow and goat milk NGS was performed in pasteurized and not pasteurized milk. The abundance profile of the indicated miRNA is shown by percentage (% of miRNA) of each miRNA, from the total miRNA reads.

TABLE 1 percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-6073 | 20.404 | 2.48165 | 12.687 | 48.946 | 6.1403 | 0.7451 | 17.062 | 8.622 | 11.765 | 30.221 |
| miR-148a-3p | 23.265 | 60.5304 | 16.089 | 7.1564 | 43.2062 | 60.9471 | 23.962 | 28.079 | 37.589 | 7.5855 |
| miR-320-3p | 3.2312 | 0.38258 | 2.6697 | 2.5783 | 0.8517 | 0.13297 | 2.6098 | 1.2201 | 0.4189 | 4.4807 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-378-3p | 0.2006 | 0.17866 | 0.153 | 0.2705 | 1.84904 | 1.28035 | 1.6041 | 1.1741 | 0.6172 | 4.3349 |
| miR-146b-5p | 0.0313 | 0.08167 | 0.0242 | 0.0825 | 1.71112 | 1.24833 | 2.5744 | 1.5413 | 3.5136 | 3.5961 |
| miR-22-3p | 0.7522 | 0.93371 | 0.3804 | 1.5888 | 1.38027 | 1.3539 | 1.0211 | 1.2205 | 1.0112 | 3.5442 |
| miR-99a-5p | 3.9096 | 1.19348 | 1.9029 | 1.0407 | 0.78121 | 0.89162 | 1.0914 | 0.0667 | 3.6809 | 3.5223 |
| let-7b-5p | 1.3099 | 0.4396 | 3.8614 | 2.394 | 0.37701 | 0.78221 | 1.8132 | 2.1639 | 1.5624 | 3.2136 |
| miR-30a-5p | 3.4282 | 7.72917 | 2.072 | 5.1547 | 3.44872 | 5.00123 | 3.3141 | 3.5 | 5.9165 | 2.7571 |
| miR-184 | 0.0009 | 0.00034 | 0.0007 | 0.0167 | 0.30201 | 0.08858 | 0.4862 | 0.904 | 0.9323 | 2.0061 |
| miR-146a-5p | 0 | 0.00064 | 0 | 0.002 | 0.00332 | 0.0009 | 0.0042 | 0.0041 | 0.7141 | 1.8258 |
| miR-22-3p | 0.3853 | 0.31685 | 0.1082 | 0.3749 | 0.23204 | 0.42575 | 0.2174 | 0.2234 | 0.4382 | 1.5718 |
| miR-423-5p | 1.3469 | 0.27955 | 0.7845 | 1.0534 | 0.93885 | 0.24646 | 1.4309 | 1.8921 | 0.3331 | 1.5224 |
| miR-30d | 3.2364 | 0.73772 | 3.8796 | 0.8305 | 2.2917 | 1.1813 | 5.0302 | 0.9273 | 1.7167 | 1.499 |
| miR-1246 | 0.3098 | 0.14808 | 0.3732 | 1.6186 | 1.19119 | 0.12359 | 4.0625 | 1.2746 | 0.3287 | 1.4086 |
| miR-6131 | 0.0215 | 0.00495 | 0.0455 | 0.1153 | 0.03968 | 0.0022 | 0.076 | 0.0605 | 0.1565 | 1.1729 |
| miR-3182 | 0.0335 | 0.00472 | 0.0269 | 0.0228 | 0.03245 | 0.00271 | 0.035 | 0.0367 | 0.6383 | 1.0624 |
| miR-1 | 0.0005 | 7.6E−05 | 0.0004 | 0.0085 | 0.10477 | 0.05023 | 0.3946 | 0.7474 | 0.633 | 1.0433 |
| miR-200a | 0.7055 | 0.98242 | 0.7094 | 0.6036 | 0.38781 | 0.41999 | 0.3216 | 0.6009 | 3.1014 | 0.9745 |
| let-7a-5p | 2.7412 | 0.73625 | 3.7304 | 1.1068 | 1.29577 | 0.85203 | 1.6843 | 3.0983 | 1.3016 | 0.9392 |
| miR-7-5p | 0.0179 | 0.03862 | 0.0182 | 0.037 | 0.17001 | 0.10585 | 0.2396 | 0.5995 | 0.4489 | 0.8404 |
| miR-99b-5p | 0.1712 | 0.01892 | 0.2312 | 0.0362 | 0.02042 | 0.00668 | 0.048 | 0.0037 | 0.4326 | 0.7761 |
| miR-181a | 0.2718 | 0.09718 | 0.199 | 0.3611 | 0.38278 | 0.26637 | 0.5616 | 0.5559 | 0.6402 | 0.7753 |
| miR-151-3p | 0.7285 | 0.37507 | 0.6872 | 0.6577 | 0.68922 | 0.38272 | 1.6614 | 0.5254 | 0.8809 | 0.7053 |
| miR-4448 | 0.2594 | 0.02277 | 1.2026 | 0.087 | 0.03308 | 0.01631 | 0.1579 | 0.0353 | 0.2521 | 0.6519 |
| miR-3135b | 0.7955 | 0.01695 | 4.6233 | 0.1421 | 0.03782 | 0.0029 | 0.1618 | 0.0474 | 0.1347 | 0.6251 |
| miR-99a-5p | 1.5511 | 0.09575 | 1.2729 | 0.9136 | 0.5687 | 0.10474 | 1.4722 | 0.1247 | 0.3177 | 0.5963 |
| miR-92b | 1.9302 | 0.28868 | 2.0273 | 0.2175 | 0.53345 | 0.34812 | 0.3062 | 0.2761 | 0.8022 | 0.5456 |
| miR-375 | 1.2239 | 0.07638 | 3.0456 | 0.3261 | 1.10159 | 0.31841 | 3.5913 | 0.2837 | 0.4876 | 0.5449 |
| miR-21-5p | 1.9407 | 7.11843 | 2.6845 | 4.2676 | 2.96058 | 3.08702 | 1.6892 | 6.6829 | 2.7673 | 0.5215 |
| miR-200c | 5.9645 | 0.33452 | 6.5194 | 2.741 | 3.60334 | 0.40346 | 5.0919 | 2.7838 | 0.5339 | 0.5188 |
| miR-7704 | 0.0001 | 0 | 0.4297 | 0.0017 | 0.00235 | 0 | 0.0043 | 0 | 0.1097 | 0.4828 |
| miR-191-5p | 0.5211 | 0.08272 | 0.1946 | 0.2905 | 0.2652 | 0.18052 | 0.2342 | 0.2388 | 0.2537 | 0.4686 |
| miR-200b | 4.1085 | 0.70986 | 3.4398 | 2.2582 | 3.74879 | 1.13101 | 3.7702 | 2.4141 | 0.7629 | 0.42 |
| miR-24-3p | 0.0765 | 0.09677 | 0.0551 | 0.1009 | 0.38926 | 0.19018 | 0.0666 | 0.471 | 0.2625 | 0.4095 |
| miR-205 | 0.0011 | 0.00121 | 0.0026 | 0.0033 | 0.00328 | 0.00057 | 0.0076 | 0.0007 | 0.2276 | 0.4063 |
| miR-4488 | 0 | 0 | 0.0014 | 0.0002 | 0 | 0 | 0 | 0 | 0.0523 | 0.3998 |
| miR-423-3p | 0.5055 | 0.04395 | 0.7089 | 0.2251 | 0.27697 | 0.1321 | 0.6442 | 0.9441 | 0.1488 | 0.381 |
| miR-26a-5p | 2.5289 | 1.54242 | 1.1602 | 1.7018 | 2.44043 | 3.46306 | 1.154 | 4.5219 | 1.1453 | 0.373 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-22-3p | 0.0903 | 0.07657 | 0.036 | 0.0589 | 0.06077 | 0.04903 | 0.0311 | 0.0304 | 0.1938 | 0.3673 |
| miR-9-5p | 0.0009 | 0.00083 | 0.0017 | 0.0027 | 0.08696 | 0.03307 | 0.1588 | 0.1802 | 0.1932 | 0.3492 |
| miR-143-3p | 0.0057 | 0.12173 | 0.009 | 0.0844 | 0.03875 | 0.01411 | 0.0512 | 0.0933 | 0.4221 | 0.303 |
| miR-27b-3p | 0.3421 | 0.43125 | 0.5542 | 0.2602 | 0.22146 | 0.34719 | 0.1081 | 0.3587 | 0.8065 | 0.2898 |
| miR-25-3p | 0.4252 | 0.16934 | 0.2312 | 0.3311 | 0.77674 | 0.36206 | 0.4127 | 0.355 | 0.3335 | 0.2829 |
| miR-193b-3p | 0 | 0 | 0 | 0.0003 | 0 | 0 | 0 | 0 | 0.0631 | 0.2824 |
| let-7i-5p | 0.129 | 0.55211 | 0.1242 | 0.4516 | 0.46389 | 1.08963 | 0.3472 | 1.3227 | 0.5548 | 0.2642 |
| miR-7641 | 0.0212 | 0.03277 | 0.1598 | 0.0227 | 0.02496 | 0.02746 | 0.0116 | 0.0631 | 0.0676 | 0.2486 |
| miR-361-3p | 0.4448 | 0.04112 | 0.2396 | 0.0491 | 0.02425 | 0.01662 | 0.0445 | 0.0104 | 0.1542 | 0.2429 |
| miR-4497 | 0.0627 | 0.0182 | 0.1607 | 0.2548 | 0.01643 | 0.0017 | 0.0245 | 0.0696 | 0.0644 | 0.23 |
| miR-186-5p | 0.2777 | 0.40513 | 0.1884 | 0.4588 | 0.2532 | 0.29726 | 0.2659 | 0.3365 | 0.1844 | 0.2297 |
| let-7c-5p | 0.4128 | 0.08405 | 0.6347 | 0.2272 | 0.13759 | 0.08441 | 0.3586 | 0.3468 | 0.2259 | 0.2228 |
| miR-193a-5p | 0.1619 | 0.00672 | 0.2504 | 0.0467 | 0.00943 | 0.00146 | 0.0173 | 0.0049 | 0.0447 | 0.2151 |
| miR-100 | 0.0072 | 0.0006 | 0.0061 | 0.0093 | 0.02396 | 0.00774 | 0.0492 | 0.0583 | 0.1292 | 0.2136 |
| miR-24-3p | 0.1232 | 0.0868 | 0.0796 | 0.1988 | 0.27727 | 0.12922 | 0.1093 | 0.464 | 0.1219 | 0.2054 |
| miR-125b | 0.2509 | 0.0114 | 0.3883 | 0.0313 | 0.04776 | 0.01414 | 0.0764 | 0.0609 | 0.1017 | 0.2044 |
| miR-148a-5p | 0.1446 | 0.02658 | 0.0761 | 0.1064 | 0.05969 | 0.03769 | 0.0964 | 0.0407 | 0.0843 | 0.2002 |
| let-7g-5p | 0.5374 | 1.21443 | 0.4328 | 0.4008 | 0.64809 | 1.89463 | 0.1928 | 0.9349 | 0.8065 | 0.193 |
| miR-4443 | 0.0194 | 0.00336 | 0.264 | 0.0599 | 0.00108 | 0.00126 | 0.0076 | 0.014 | 0.0274 | 0.1878 |
| miR-27a-3p | 0.063 | 0.13951 | 0.0605 | 0.0655 | 0.10916 | 0.10012 | 0.0322 | 0.2635 | 0.3219 | 0.1835 |
| miR-1839 | 0.0449 | 0.14778 | 0.0333 | 0.07 | 0.03036 | 0.02491 | 0.0155 | 0.0268 | 0.2524 | 0.1805 |
| miR-140-3p | 0.0787 | 0.14196 | 0.0426 | 0.1795 | 0.4143 | 0.13849 | 0.0911 | 0.5629 | 0.0922 | 0.1788 |
| miR-191 | 0.3576 | 0.02684 | 0.2643 | 0.2364 | 0.33599 | 0.05929 | 0.4308 | 0.1844 | 0.08 | 0.1652 |
| let-7f-5p | 0.5789 | 1.37229 | 0.8134 | 0.2124 | 0.65975 | 1.11127 | 0.3855 | 2.527 | 1.0279 | 0.1587 |
| miR-29a-3p | 0.0649 | 0.10806 | 0.0471 | 0.0809 | 0.05376 | 0.09972 | 0.0187 | 0.067 | 0.2095 | 0.1572 |
| miR-30c-5p | 0.0902 | 0.0424 | 0.0569 | 0.0624 | 0.14031 | 0.11859 | 0.1157 | 0.1032 | 0.1679 | 0.146 |
| miR-33a-5p | 0 | 0 | 0 | 0 | 0.01662 | 0.00552 | 0.0228 | 0.0402 | 0.092 | 0.1416 |
| miR-23b-3p | 0.1075 | 0.07623 | 0.0389 | 0.0273 | 0.09713 | 0.02031 | 0.0337 | 0.0371 | 0.1403 | 0.1383 |
| miR-652 | 0.2344 | 0.06539 | 0.2653 | 0.2029 | 0.44318 | 0.14256 | 0.2393 | 0.6364 | 0.0591 | 0.1326 |
| miR-200a | 0.6045 | 0.91657 | 0.3801 | 0.6165 | 0.66094 | 1.23538 | 0.4578 | 1.0993 | 0.6032 | 0.1224 |
| miR-100-5p | 0.0084 | 0.00328 | 0.0049 | 0.003 | 0.00816 | 0.0034 | 0.0096 | 0.0117 | 0.1252 | 0.1202 |
| miR-141 | 0.0722 | 0.12686 | 0.0917 | 0.0644 | 0.03983 | 0.06614 | 0.0288 | 0.1002 | 0.2617 | 0.1185 |
| miR-190b | 0 | 0 | 0 | 0.0001 | 0.02895 | 0.00598 | 0.0372 | 0.0657 | 0.0695 | 0.117 |
| miR-224-5p | 0.0012 | 0.0003 | 0.0003 | 0.0003 | 0.07422 | 0.12178 | 0.0811 | 0.0195 | 0.2595 | 0.1167 |
| miR-181b-5p | 0.0853 | 0.01261 | 0.0732 | 0.0629 | 0.03245 | 0.01932 | 0.0658 | 0.038 | 0.1595 | 0.1165 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-532-5p | 0.5031 | 0.27404 | 0.2614 | 0.2909 | 0.29694 | 0.24307 | 0.2995 | 0.1095 | 0.2542 | 0.1157 |
| miR-23a | 0.1961 | 0.14634 | 0.0692 | 0.124 | 0.42499 | 0.10332 | 0.0748 | 0.2569 | 0.1024 | 0.1063 |
| miR-148b-3p | 0.0868 | 0.22865 | 0.0575 | 0.0443 | 0.17276 | 0.34123 | 0.0663 | 0.2066 | 0.324 | 0.0998 |
| miR-28-3p | 0 | 0 | 0.0008 | 0.0001 | 7.5E-05 | 0 | 1E-04 | 0.0003 | 0.0569 | 0.0991 |
| miR-140 | 0.0733 | 0.10636 | 0.0512 | 0.1139 | 0.1731 | 0.07004 | 0.0329 | 0.2057 | 0.0828 | 0.0969 |
| miR-210 | 0.0073 | 0.00412 | 0.0046 | 0.0142 | 0.02642 | 0.01053 | 0.0295 | 0.0402 | 0.0539 | 0.0951 |
| miR-30e-5p | 0.1025 | 0.25055 | 0.0666 | 0.2016 | 0.20536 | 0.2988 | 0.0941 | 0.3023 | 0.2171 | 0.0941 |
| miR-4532 | 0.0622 | 0.00427 | 0.3627 | 0.0267 | 0.02973 | 0.00059 | 0.0082 | 0.0057 | 0.0283 | 0.0894 |
| miR-378c | 0.0023 | 0.00238 | 0.0008 | 0.0024 | 0.00738 | 0.01243 | 0.0085 | 0.0069 | 0.0077 | 0.0889 |
| miR-320b | 0.0539 | 0.00642 | 0.0307 | 0.0326 | 0.00484 | 0.0022 | 0.0271 | 0.01 | 0.0076 | 0.0864 |
| miR-6510-3p | 0 | 0 | 0 | 0 | 0 | 0 | 0 | 0 | 0.0156 | 0.0852 |
| miR-125b-3p | 0.0211 | 0.01265 | 0.019 | 0.0147 | 0.00671 | 0.00338 | 0.012 | 0.0031 | 0.0573 | 0.0849 |
| miR-125b-5p | 0.124 | 0.01423 | 0.1009 | 0.0068 | 0.0117 | 0.00728 | 0.0154 | 0.0147 | 0.0599 | 0.0842 |
| miR-221-3p | 0.0141 | 0.0236 | 0.0005 | 0.0354 | 0.05246 | 0.02371 | 0.0058 | 0.038 | 0.0647 | 0.082 |
| miR-2340 | 0.0304 | 0.00415 | 0.0936 | 0.0091 | 0.05738 | 0.00246 | 0.0265 | 0.0059 | 0.0302 | 0.0777 |
| miR-10a-5p | 0.0009 | 0.00302 | 0.0012 | 0.0022 | 0.0165 | 0.00646 | 0.0192 | 0.0304 | 0.0519 | 0.0757 |
| miR-320c | 0.0225 | 0.00581 | 0.0049 | 0.0146 | 0.00205 | 0.00172 | 0.009 | 0.0047 | 0.0066 | 0.07 |
| miR-369-3p | 0.0316 | 0.01616 | 0.0105 | 0.0007 | 0.02355 | 0.00962 | 0.0012 | 0.0029 | 0.0114 | 0.0676 |
| miR-30b-5p | 0.1167 | 0.1975 | 0.0442 | 0.1561 | 0.23032 | 0.27472 | 0.4944 | 0.1902 | 0.1848 | 0.0606 |
| miR-361-3p | 0.2239 | 0.0171 | 0.1746 | 0.0356 | 0.0481 | 0.02417 | 0.0674 | 0.0207 | 0.0438 | 0.0603 |
| miR-1307-3p | 0.0997 | 0.00759 | 0.1082 | 0.0501 | 0.04571 | 0.00986 | 0.0572 | 0.0888 | 0.0156 | 0.0603 |
| miR-222-3p | 0.0043 | 0.00812 | 0.0017 | 0.0182 | 0.01095 | 0.00792 | 0.0061 | 0.0217 | 0.0371 | 0.0603 |
| miR-574-3p | 0.5334 | 0.05497 | 0.2014 | 0.0573 | 0.31304 | 0.09261 | 0.1405 | 0.0486 | 0.0541 | 0.0589 |
| miR-3196 | 0 | 0 | 0 | 0 | 0 | 0 | 0 | 0 | 0.0058 | 0.0569 |
| miR-200a-5p | 0.0743 | 0.02201 | 0.0761 | 0.0592 | 0.09378 | 0.05963 | 0.1586 | 0.0867 | 0.0436 | 0.0559 |
| miR-1307-5p | 0.0001 | 0.00034 | 0 | 0.0003 | 0.0003 | 0.00013 | 0.0001 | 0.0014 | 0.0038 | 0.0526 |
| miR-125a-5p | 0.0906 | 0.01019 | 0.0567 | 0.0056 | 0.00436 | 0.00393 | 0.0034 | 0.0022 | 0.0385 | 0.0522 |
| miR-4516 | 0 | 0 | 0.0017 | 0.0001 | 0 | 0 | 0 | 0 | 0.0068 | 0.0509 |
| miR-423-3p | 0.0548 | 0.0051 | 0.0751 | 0.0233 | 0.02764 | 0.01313 | 0.0621 | 0.0539 | 0.0154 | 0.0504 |
| miR-182 | 0.0875 | 0.03387 | 0.0663 | 0.0533 | 0.02705 | 0.01017 | 0.0439 | 0.0324 | 0.0705 | 0.0494 |
| miR-345-5p | 0 | 0 | 0 | 0 | 0 | 0 | 0 | 0 | 0.0093 | 0.0469 |
| miR-629-5p | 0 | 0 | 0 | 0 | 0 | 0 | 1E-04 | 0 | 0.0121 | 0.0459 |
| miR-122 | 0.0212 | 0.03828 | 0.9063 | 0.2655 | 0.10801 | 0.00879 | 0.304 | 0.1523 | 0.0061 | 0.045 |
| miR-133a-3p | 0 | 0 | 0 | 0.0004 | 0.0108 | 0.00367 | 0.0104 | 0.0127 | 0.0258 | 0.045 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-425-5p | 0.0277 | 0.00627 | 0.0221 | 0.0523 | 0.00663 | 0.00247 | 0.009 | 0.0191 | 0.0156 | 0.0442 |
| miR-19b-3p | 0.0073 | 0.04867 | 0.0066 | 0.0421 | 0.03778 | 0.02524 | 0.0118 | 0.0883 | 0.0385 | 0.0427 |
| let-7d-3p | 0.0321 | 0.00925 | 0.0413 | 0.01 | 0.01025 | 0.00768 | 0.0052 | 0.003 | 0.0483 | 0.0422 |
| miR-4492 | 0.0201 | 0.00298 | 3.3496 | 0.0477 | 0.00462 | 0.0003 | 0.0388 | 0.0233 | 0.0068 | 0.042 |
| miR-452-5p | 0 | 0 | 0 | 0.0003 | 0.01796 | 0.01006 | 0.0234 | 0.0174 | 0.0096 | 0.04 |
| let-7d-5p | 0.0984 | 0.01971 | 0.0905 | 0.0492 | 0.05849 | 0.0315 | 0.0563 | 0.1493 | 0.0429 | 0.0387 |
| miR-93-5p | 0.0343 | 0.04633 | 0.0134 | 0.1202 | 0.2257 | 0.07464 | 0.0549 | 0.2155 | 0.0283 | 0.0363 |
| miR-106b-3p | 0.0361 | 0.0105 | 0.0181 | 0.0258 | 0.01144 | 0.00726 | 0.0091 | 0.0164 | 0.0324 | 0.0363 |
| miR-378i | 0.002 | 0.00113 | 0.0017 | 0.0028 | 0.0168 | 0.01099 | 0.0141 | 0.0113 | 0.0043 | 0.0358 |
| miR-125a | 0.0633 | 0.00204 | 0.0901 | 0.0124 | 0.00708 | 0.00127 | 0.0082 | 0.007 | 0.0146 | 0.0335 |
| miR-668-3p | 0.0005 | 0.00011 | 0.0017 | 0 | 0.00093 | 0.00065 | 0.0003 | 0 | 0.0059 | 0.0325 |
| miR-101-3p | 0.0218 | 0.28604 | 0.0374 | 0.0304 | 0.03666 | 0.09098 | 0.0213 | 0.1072 | 0.2151 | 0.032 |
| miR-378c | 0.0005 | 0.00079 | 0 | 0.0002 | 0.00272 | 0.00691 | 0.0021 | 0.0022 | 0.0035 | 0.0315 |
| miR-185 | 0.0165 | 0.01397 | 0.0338 | 0.0448 | 0.03677 | 0.02225 | 0.0412 | 0.0874 | 0.0071 | 0.0313 |
| miR-30a-3p | 0.06 | 0.02632 | 0.0984 | 0.0747 | 0.02224 | 0.02 | 0.0545 | 0.031 | 0.0698 | 0.0313 |
| miR-16-5p | 0.0014 | 0.02061 | 0.0004 | 0.0076 | 0.00142 | 0.00037 | 0 | 0.0005 | 0.0302 | 0.031 |
| miR-3656 | 0 | 0 | 0 | 0 | 0 | 0 | 0 | 0 | 0.0014 | 0.0305 |
| miR-142-5p | 0.0178 | 0.08918 | 0.0012 | 0.0908 | 0.32671 | 0.15079 | 0.0663 | 0.3196 | 0.043 | 0.0291 |
| miR-101 | 0.0201 | 0.29794 | 0.0551 | 0.0432 | 0.06077 | 0.15423 | 0.0298 | 0.1867 | 0.2364 | 0.0283 |
| miR-192-5p | 0.0111 | 0.03334 | 0.0108 | 0.0279 | 0.02124 | 0.04897 | 0.0174 | 0.0452 | 0.0332 | 0.0283 |
| miR-223-3p | 0.0291 | 0.18969 | 0.0022 | 0.4222 | 0.80424 | 0.63877 | 0.0584 | 0.6511 | 0.0531 | 0.0278 |
| miR-146a | 0.0004 | 0.01563 | 0 | 0.0056 | 0.00115 | 0.00659 | 0.0014 | 0.0037 | 0.0552 | 0.0271 |
| miR-4508 | 0.016 | 0.00211 | 1.3053 | 0.0176 | 0.00708 | 0.00052 | 0.0248 | 0.0224 | 0.0036 | 0.0271 |
| miR-103-3p | 0.1433 | 0.05275 | 0.1769 | 0.229 | 0.41169 | 0.17603 | 0.3552 | 0.4156 | 0.0296 | 0.0268 |
| miR-29a | 0.0253 | 0.01382 | 0.0211 | 0.0311 | 0.03029 | 0.03084 | 0.023 | 0.0374 | 0.0312 | 0.0243 |
| miR-151-5p | 0.0195 | 0.00698 | 0.1152 | 0.0199 | 0.01442 | 0.0412 | 0.0659 | 0.0147 | 0.0242 | 0.0226 |
| miR-429 | 0 | 7.6E-05 | 0 | 0 | 0 | 0 | 0 | 0.0002 | 0.0675 | 0.0216 |
| miR-320d | 0.0082 | 0.00076 | 0.0056 | 0.006 | 0.00205 | 0.00022 | 0.0051 | 0.0016 | 0.002 | 0.0206 |
| miR-99b-3p | 0.0003 | 0.00087 | 0.0003 | 0.0003 | 0 | 0 | 0 | 0 | 0.012 | 0.0206 |
| let-7i-3p | 0.0005 | 0.00034 | 0.0004 | 0.0003 | 0.00075 | 0.00057 | 0 | 0.0009 | 0.0056 | 0.0199 |
| miR-378d | 0.0009 | 0.00064 | 0.0005 | 0.0008 | 0.00577 | 0.00284 | 0.003 | 0.0016 | 0.0019 | 0.0194 |
| miR-183 | 0.015 | 0.01522 | 0.0131 | 0.0094 | 0.00529 | 0.00824 | 0.0038 | 0.0088 | 0.0473 | 0.0186 |
| miR-23b-3p | 0.0693 | 0.00782 | 0.026 | 0.014 | 0.09549 | 0.0166 | 0.0285 | 0.0275 | 0.0197 | 0.0181 |
| miR-146b-3p | 0 | 0 | 0 | 0 | 0 | 0 | 0 | 0 | 0.009 | 0.0181 |
| miR-3615 | 0 | 0 | 0 | 0 | 0 | 0 | 0 | 0 | 0.0044 | 0.0176 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-107-3p | 0.0188 | 0.01533 | 0.0103 | 0.0197 | 0.02325 | 0.02726 | 0.0146 | 0.0266 | 0.018 | 0.0166 |
| miR-182 | 0.0045 | 0.01091 | 0.0069 | 0.0049 | 0.00123 | 0.00068 | 0.0019 | 0.0021 | 0.0334 | 0.0161 |
| miR-22-5p | 0.0305 | 0.02065 | 0.0211 | 0.0151 | 0.00715 | 0.01317 | 0.0051 | 0.0117 | 0.0344 | 0.0159 |
| miR-335 | 0.0003 | 0.00023 | 0 | 0.0001 | 0.0019 | 0.00109 | 0.0003 | 0.0044 | 0.0229 | 0.0151 |
| miR-203a-3p | 0.0515 | 0.06902 | 0.0325 | 0.0745 | 0.00768 | 0.00211 | 0.0087 | 0.0046 | 0.0272 | 0.0149 |
| miR-21-3p | 0 | 0 | 0 | 0 | 0 | 0 | 0 | 0 | 0.0085 | 0.0144 |
| miR-378d | 0 | 7.6E−05 | 0.0004 | 0.0002 | 0.00156 | 0.00133 | 0.0013 | 0.0012 | 0.0017 | 0.0144 |
| miR-589-5p | 0 | 0 | 0 | 0 | 0 | 0 | 0 | 0 | 0.0033 | 0.0142 |
| miR-6869-5p | 0 | 0 | 0 | 0 | 0 | 0 | 0 | 0 | 0.0019 | 0.0139 |
| miR-2110 | 0 | 0 | 0 | 0 | 0 | 0 | 0 | 0 | 0.0014 | 0.0137 |
| miR-26b-5p | 0.1107 | 0.26784 | 0.1568 | 0.0824 | 0.14497 | 0.62337 | 0.0458 | 0.6869 | 0.0544 | 0.0134 |
| miR-181a-2-3p | 0.0196 | 0.00287 | 0.0321 | 0.0058 | 0.00261 | 0.00074 | 0.0156 | 0.0002 | 0.0116 | 0.0134 |
| miR-664a-5p | 0 | 0 | 0 | 0 | 0 | 0 | 0 | 0 | 0.0018 | 0.0134 |
| miR-192 | 0.003 | 0.00827 | 0.0082 | 0.0174 | 0.01237 | 0.03893 | 0.0128 | 0.0561 | 0.0127 | 0.0129 |
| miR-452 | 0 | 0.00019 | 0 | 0.0004 | 0.0063 | 0.00401 | 0.0058 | 0.0038 | 0.0032 | 0.0129 |
| miR-21-5p | 0.0746 | 0.15873 | 0.084 | 0.3238 | 0.10194 | 0.11128 | 0.1167 | 0.3736 | 0.0557 | 0.0127 |
| miR-193a-3p | 0.0002 | 0.00219 | 0 | 0.0002 | 7.5E−05 | 0.00066 | 0 | 0 | 0.0049 | 0.0124 |
| miR-425-3p | 0.0029 | 0.00166 | 0.002 | 0.0068 | 0.00298 | 0.00087 | 0.0032 | 0.0027 | 0.0034 | 0.0122 |
| miR-339-3p | 0 | 0 | 0 | 0 | 0 | 0 | 0 | 0 | 0.0019 | 0.0122 |
| miR-125a-3p | 0.011 | 0.00215 | 0.013 | 0.0027 | 0.0022 | 0.0005 | 0.0017 | 0.0007 | 0.0034 | 0.0117 |
| miR-941 | 0 | 0 | 0 | 0 | 0 | 0 | 0 | 0 | 0.0011 | 0.0117 |
| let-7b-3p | 0.0289 | 0.01076 | 0.0168 | 0.0047 | 0.00633 | 0.00853 | 0.0052 | 0.0027 | 0.0156 | 0.0114 |
| miR-106b-3p | 0.0311 | 0.00748 | 0.0205 | 0.0348 | 0.02902 | 0.00728 | 0.0358 | 0.0266 | 0.0091 | 0.0112 |
| miR-152 | 0.0289 | 0.0421 | 0.0209 | 0.0366 | 0.03513 | 0.0443 | 0.0311 | 0.0465 | 0.0154 | 0.0112 |
| miR-224 | 0 | 0 | 0 | 0.0002 | 0.02303 | 0.00417 | 0.0377 | 0.0039 | 0.019 | 0.0107 |
| let-7e-5p | 0.0294 | 0.0122 | 0.0419 | 0.0195 | 0.01516 | 0.0123 | 0.0244 | 0.0524 | 0.0151 | 0.0107 |
| miR-378e | 0.0005 | 0.00038 | 0.0003 | 0.0006 | 0.00488 | 0.00345 | 0.0058 | 0.0037 | 0.0009 | 0.0107 |
| miR-484 | 0.0496 | 0.01019 | 0.0514 | 0.0078 | 0.018 | 0.01115 | 0.0099 | 0.0083 | 0.0186 | 0.0104 |
| miR-502a | 0.0036 | 0.00313 | 0.0022 | 0.0051 | 0.00067 | 0.0007 | 0.0006 | 0.0002 | 0.0061 | 0.0104 |
| miR-128-3p | 0.0191 | 0.00793 | 0.0322 | 0.0077 | 0.01386 | 0.04389 | 0.0159 | 0.0058 | 0.0377 | 0.0102 |
| miR-17-5p | 0.0094 | 0.01061 | 0.0112 | 0.0261 | 0.03111 | 0.01182 | 0.0117 | 0.0333 | 0.0103 | 0.0099 |
| miR-197-3p | 0.0266 | 0.00721 | 0.0179 | 0.0057 | 0.04165 | 0.01906 | 0.0153 | 0.022 | 0.0155 | 0.0094 |
| miR-378-5p | 0.0042 | 0.00023 | 0.0029 | 0.0007 | 0.00842 | 0.00312 | 0.0128 | 0.0027 | 0.0029 | 0.0092 |
| miR-28-5p | 0.0062 | 0.00261 | 0.0062 | 0.0133 | 0.01382 | 0.00425 | 0.0165 | 0.013 | 0.0051 | 0.0087 |
| miR-132 | 0.0008 | 0.00106 | 0.0005 | 0.0008 | 0.00373 | 0.00078 | 0 | 0.0008 | 0.009 | 0.0087 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-223-5p | 0.0015 | 0.00619 | 0.0003 | 0.03 | 0.72536 | 0.23699 | 0.0574 | 1.1574 | 0.0071 | 0.0084 |
| miR-339b | 0.1335 | 0.02058 | 0.1264 | 0.0174 | 0.09575 | 0.03401 | 0.0382 | 0.0093 | 0.0206 | 0.0082 |
| let-7d-3p | 0.013 | 0.0048 | 0.0176 | 0.0059 | 0.02075 | 0.01357 | 0.0108 | 0.008 | 0.0077 | 0.0082 |
| miR-27a-5p | 0.0025 | 0.00276 | 0.0048 | 0.0084 | 0.0146 | 0.0036 | 0.0052 | 0.0088 | 0.0046 | 0.0082 |
| miR-30e-3p | 0.0083 | 0.00902 | 0.0147 | 0.0094 | 0.01531 | 0.01252 | 0.0108 | 0.0528 | 0.026 | 0.0079 |
| miR-27a-3p | 0.0021 | 0.00974 | 0.0016 | 0.0044 | 0.00969 | 0.01765 | 0.0025 | 0.0487 | 0.0077 | 0.0077 |
| miR-542-3p | 0.0262 | 0.0074 | 0.0286 | 0.0009 | 0.00596 | 0.00198 | 0.0012 | 0.0023 | 0.0057 | 0.0077 |
| miR-23a | 0.0325 | 0.01136 | 0.0213 | 0.0187 | 0.16788 | 0.05617 | 0.0254 | 0.0879 | 0.0059 | 0.0075 |
| miR-660-5p | 0 | 0.00026 | 0 | 0 | 7.5E-05 | 0.0003 | 0 | 0 | 0.0098 | 0.0075 |
| miR-361-5p | 0.013 | 0.00834 | 0.009 | 0.0067 | 0.03573 | 0.01106 | 0.008 | 0.0118 | 0.0133 | 0.0072 |
| miR-378g | 0.0009 | 0.0003 | 0.0008 | 0.0004 | 0.00577 | 0.0038 | 0.0049 | 0.004 | 0.0012 | 0.0072 |
| miR-324-3p | 0.0018 | 0.00034 | 0.0017 | 0.0014 | 0.00115 | 0.0007 | 0.0034 | 0.0018 | 0.0016 | 0.0072 |
| miR-1307-5p | 0 | 7.6E-05 | 0 | 0.0003 | 0.00115 | 0.00044 | 0.0005 | 0.0012 | 0.0018 | 0.0072 |
| miR-30a-3p | 0.0388 | 0.00748 | 0.0966 | 0.0435 | 0.04504 | 0.0185 | 0.119 | 0.0588 | 0.0199 | 0.007 |
| miR-934 | 0 | 0 | 0 | 0 | 0 | 0 | 0 | 0 | 0.0071 | 0.007 |
| miR-16b | 0.0033 | 0.01635 | 0.0016 | 0.0029 | 0.00205 | 0.00065 | 0.0001 | 0.0018 | 0.0086 | 0.0067 |
| miR-4330 | 0.0028 | 0.00034 | 0.013 | 0.0002 | 0.0019 | 0.00024 | 0.0003 | 0.0006 | 0.0045 | 0.0067 |
| miR-181a-3p | 0.0003 | 0.00026 | 0.0004 | 0.0005 | 0.00537 | 0.00107 | 0.0101 | 0.0015 | 0.0029 | 0.0065 |
| miR-24-2-5p | 0.0025 | 0.00219 | 0.0027 | 0.0033 | 0.00682 | 0.00247 | 0.0047 | 0.0058 | 0.0024 | 0.0065 |
| miR-365-3p | 0.0099 | 0.00532 | 0.003 | 0.001 | 0.00119 | 0.00172 | 0 | 0 | 0.0111 | 0.0062 |
| miR-500-3p | 0.0134 | 0.01057 | 0.0064 | 0.0168 | 0.00652 | 0.00471 | 0.0048 | 0.0048 | 0.0048 | 0.0057 |
| miR-206 | 0 | 0 | 0 | 0 | 0.00052 | 0.00024 | 0.0019 | 0.0042 | 0.0024 | 0.0057 |
| miR-155-5p | 0.0121 | 0.00865 | 0.0104 | 0.0119 | 0.10771 | 0.08188 | 0.1359 | 0.1151 | 0.0076 | 0.0055 |
| miR-328-3p | 0.008 | 0.0014 | 0.0137 | 0.002 | 0.01025 | 0.00713 | 0.0046 | 0.0046 | 0.0031 | 0.0055 |
| miR-4286 | 0.0027 | 0.00026 | 0.0027 | 0.0003 | 0.00168 | 0.00015 | 0.0002 | 0.0003 | 0.0011 | 0.0055 |
| miR-494 | 0.0014 | 0.0003 | 0 | 0.0002 | 0.00995 | 0.00722 | 0.0125 | 0.0064 | 0.0016 | 0.0052 |
| miR-30c-2-3p | 0.0142 | 0.00332 | 0.0176 | 0.0142 | 7.5E-05 | 0 | 0 | 0.0002 | 0.0047 | 0.0052 |
| miR-16b-5p | 0.004 | 0.00921 | 0.0009 | 0.0017 | 0.44463 | 0.12367 | 0.0762 | 0.4422 | 0.0134 | 0.005 |
| miR-744 | 0.0058 | 0.00125 | 0.0108 | 0.0109 | 0.03782 | 0.00787 | 0.0455 | 0.0759 | 0.0016 | 0.005 |
| miR-150 | 0.0066 | 0.00419 | 0.0016 | 0.0043 | 0.01513 | 0.00336 | 0.0008 | 0.0004 | 0.0027 | 0.005 |
| miR-6724-5p | 0.0007 | 0.00042 | 0.0623 | 0.0017 | 0.00089 | 0 | 0.0024 | 0.0031 | 0.0007 | 0.005 |
| miR-5787 | 0.0061 | 0.00094 | 0.078 | 0.0164 | 0.00391 | 0.00028 | 0.0095 | 0.0056 | 0.0021 | 0.0047 |
| miR-20a-5p | 0.0192 | 0.05531 | 0.0307 | 0.0326 | 0.04903 | 0.03616 | 0.0124 | 0.0746 | 0.0212 | 0.0045 |
| miR-29c | 0.0059 | 0.03073 | 0.0048 | 0.0098 | 0.00436 | 0.00999 | 0.0015 | 0.0087 | 0.008 | 0.0042 |
| miR-335-5p | 0.0001 | 0 | 0 | 0 | 0.00022 | 0.00028 | 0.0002 | 0.0002 | 0.0121 | 0.0042 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-99b-3p | 0.0009 | 0 | 0.001 | 0.0008 | 0.00048 | 7.4E-05 | 0.0011 | 0.0003 | 0.002 | 0.0042 |
| miR-339-5p | 0.0014 | 7.6E-05 | 0.0007 | 0 | 0.00037 | 0.00031 | 0 | 0.0002 | 0.0007 | 0.0042 |
| miR-29c-5p | 0.0072 | 0.01389 | 0.0029 | 0.0037 | 0.00302 | 0.00436 | 0.0023 | 0.0021 | 0.0049 | 0.004 |
| miR-335-3p | 0.0004 | 0 | 0.0008 | 0 | 0.00048 | 0.00098 | 0.0006 | 0 | 0.0263 | 0.0037 |
| miR-2904 | 0.0007 | 0.00042 | 0.0212 | 0.0004 | 0.00246 | 0.00024 | 0.0087 | 0.2565 | 0.0015 | 0.0035 |
| miR-28 | 0.003 | 0.00166 | 0.004 | 0.0097 | 0.00939 | 0.00264 | 0.0084 | 0.0119 | 0.0016 | 0.0035 |
| miR-2478 | 0.0113 | 0.00064 | 0.0294 | 0.0046 | 0.00417 | 0.00089 | 0.0133 | 0.0048 | 0.0041 | 0.0035 |
| miR-760-3p | 0.0165 | 0.00166 | 0.0114 | 0.0046 | 0.00149 | 0.00037 | 0.0017 | 0.0009 | 0.0009 | 0.0035 |
| miR-147 | 0.0003 | 0.00253 | 0 | 0.0081 | 0.00209 | 0.00194 | 0.0004 | 0.0117 | 0.0007 | 0.0035 |
| miR-183 | 0.0023 | 0.00174 | 0.0035 | 0.0044 | 0.00209 | 0.00065 | 0.0022 | 0.0025 | 0.0034 | 0.0035 |
| miR-885 | 0.039 | 0.0097 | 0.0138 | 0.0042 | 0.01945 | 0.02687 | 0.0106 | 0.0061 | 0.0152 | 0.0032 |
| miR-30e-3p | 0.0037 | 0.002 | 0.0082 | 0.0047 | 0.0133 | 0.00646 | 0.0181 | 0.0492 | 0.0065 | 0.0032 |
| miR-15b-5p | 0.0014 | 0.00914 | 0.0018 | 0.0037 | 0.01077 | 0.00654 | 0.0003 | 0.016 | 0.0067 | 0.0032 |
| miR-200b-5p | 0.0678 | 0.00914 | 0.1608 | 0.0471 | 0.04188 | 0.01145 | 0.1448 | 0.0394 | 0.0073 | 0.003 |
| miR-223-5p | 0.001 | 0.008 | 0 | 0.0077 | 0 | 9.2E-05 | 0 | 0.0002 | 0.0068 | 0.003 |
| miR-532-3p | 0.0043 | 0.00189 | 0.0029 | 0.003 | 0.00056 | 0.00039 | 0.0003 | 0.0005 | 0.0014 | 0.003 |
| miR-7977 | 0.0096 | 0.00091 | 0.0118 | 0.0017 | 0.00138 | 0 | 0.0022 | 0.0039 | 0.0024 | 0.0027 |
| miR-194 | 0.0055 | 0.00544 | 0.0069 | 0.0127 | 0.01971 | 0.00945 | 0.0123 | 0.029 | 0.0021 | 0.0025 |
| miR-339a | 0.0656 | 0.00683 | 0.081 | 0.0066 | 0.05794 | 0.02399 | 0.0282 | 0.0104 | 0.0083 | 0.0022 |
| miR-374b-5p | 0.0133 | 0.0205 | 0.0118 | 0.0069 | 0.02507 | 0.02559 | 0.0046 | 0.0254 | 0.0162 | 0.0022 |
| miR-671-5p | 0.0003 | 0.00049 | 0 | 0.0011 | 0.00164 | 0.00068 | 0.001 | 0.0015 | 0.0003 | 0.0022 |
| miR-378f | 0.0001 | 0.00034 | 0.0003 | 0.0004 | 0.00171 | 0.0012 | 0.0006 | 0.0012 | 0.0005 | 0.0022 |
| miR-10a | 0.0001 | 0.00068 | 0 | 0.0011 | 0.00224 | 0.00026 | 0.0031 | 0.0016 | 0.0028 | 0.0022 |
| miR-145-5p | 0.0004 | 0.00049 | 0 | 0.0006 | 0.00048 | 9.2E-05 | 0.0008 | 0.0009 | 0.0009 | 0.0022 |
| miR-660 | 0.2234 | 0.2228 | 0.1122 | 0.1977 | 0.08252 | 0.07809 | 0.074 | 0.0481 | 0.0803 | 0.002 |
| miR-181b | 0.0098 | 0.00083 | 0.0096 | 0.0042 | 0.00369 | 0.00135 | 0.005 | 0.0029 | 0.0023 | 0.002 |
| miR-124a | 0 | 0 | 0 | 0 | 0.00022 | 0.00013 | 0.0005 | 0.0011 | 0.0009 | 0.002 |
| miR-28-3p | 0.0654 | 0.01631 | 0.0875 | 0.0349 | 0.07798 | 0.02777 | 0.1117 | 0.0217 | 0.0058 | 0.0017 |
| miR-135a | 0.0008 | 0.00117 | 0.0022 | 0.0012 | 0.01818 | 0.00774 | 0.0093 | 0.0336 | 0.0026 | 0.0017 |
| miR-499-5p | 0.0024 | 0.00959 | 0.0027 | 0.0024 | 0.00376 | 0.00901 | 0.0029 | 0.0084 | 0.0077 | 0.0017 |
| miR-29b | 0.0057 | 0.0054 | 0.0095 | 0.015 | 0.00455 | 0.0079 | 0.0035 | 0.0085 | 0.0025 | 0.0017 |
| miR-421-3p | 0.0026 | 0.00253 | 0.0009 | 0.004 | 0.00317 | 0.0019 | 0.0007 | 0.0029 | 0.0016 | 0.0017 |
| miR-365b-5p | 0.001 | 7.6E-05 | 0.0033 | 0.0004 | 0 | 0 | 0.0004 | 0 | 0 | 0.0017 |
| miR-5100 | 0.001 | 7.6E-05 | 0.0009 | 0 | 0.00011 | 0.00022 | 0.0004 | 0.0003 | 0.0001 | 0.0017 |
| miR-98-5p | 0.0238 | 0.02583 | 0.0289 | 0.0096 | 0.02843 | 0.06304 | 0.0121 | 0.073 | 0.008 | 0.0015 |
| miR-221-3p | 0.0029 | 0.00253 | 0.0012 | 0.0143 | 0.06926 | 0.02785 | 0.0118 | 0.0789 | 0.0034 | 0.0015 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-106b-5p | 0.0008 | 0.00725 | 0.0023 | 0.0056 | 0.00283 | 0.00711 | 0.0007 | 0.0137 | 0.0031 | 0.0015 |
| miR-25-5p | 0.003 | 0.00019 | 0.002 | 0.0012 | 0.00089 | 5.5E−05 | 0.0023 | 0.0015 | 0.0004 | 0.0015 |
| miR-1261 | 0.0002 | 0.00034 | 0.001 | 0.0016 | 0.00015 | 0.00011 | 0.0001 | 0.005 | 0.0009 | 0.0012 |
| miR-4302 | 0.0002 | 7.6E−05 | 0.0005 | 0.0014 | 0.00056 | 0 | 0.002 | 0.0002 | 0.0001 | 0.0012 |
| miR-16a | 0.0139 | 0.06049 | 0.0062 | 0.0114 | 0.00294 | 0.00299 | 1E−04 | 0.0021 | 0.0036 | 0.001 |
| miR-326-3p | 0.0099 | 0.00412 | 0.0047 | 0.0069 | 0.01654 | 0.0075 | 0.008 | 0.0081 | 0.0019 | 0.001 |
| miR-92b | 0.0203 | 0.0017 | 0.0208 | 0.0008 | 0.00376 | 0.00138 | 0.0018 | 0.0017 | 0.0045 | 0.001 |
| miR-338-5p | 0.0007 | 0.00147 | 0 | 0.0052 | 0.00183 | 0.00063 | 0.0008 | 0.0011 | 0.0005 | 0.001 |
| miR-671-3p | 0.0008 | 0 | 0.0018 | 0 | 0.00019 | 0.00015 | 0.0007 | 0.0002 | 0.0001 | 0.001 |
| miR-34a | 0.0005 | 0.00117 | 0.0003 | 0.0006 | 0.00034 | 7.4E−05 | 1E−04 | 0 | 0.0009 | 0.001 |
| miR-30b-3p | 0.001 | 0 | 0.0029 | 0.0014 | 0.00022 | 0.00011 | 0.0011 | 0.0011 | 0 | 0.001 |
| miR-342-3p | 0.001 | 0.00125 | 0.001 | 0.0025 | 0.00063 | 0.00031 | 0.0005 | 0.0002 | 0.0001 | 0.0007 |
| miR-92a-1-5p | 0.0042 | 0.00011 | 0.0016 | 0.0004 | 0 | 0 | 0 | 0 | 0.0006 | 0.0007 |
| miR-22-5p | 0.0014 | 0.00049 | 0.0012 | 0.0013 | 0.00067 | 0.00041 | 0.0003 | 0.001 | 0.0004 | 0.0007 |
| miR-199c-3p | 0 | 7.6E−05 | 0 | 0.0004 | 7.5E−05 | 0 | 0 | 0 | 0.0078 | 0.0007 |
| miR-196a | 0.0007 | 0.00079 | 0.0017 | 0.0003 | 0 | 5.5E−05 | 0.0001 | 0.0002 | 0.0009 | 0.0007 |
| miR-6832-3p | 0 | 0 | 0 | 0 | 0.00048 | 0.00013 | 0.0006 | 0.0004 | 0.0006 | 0.0007 |
| miR-16a-5p | 0.0007 | 0.00261 | 0.0007 | 0.0008 | 1.29078 | 0.34659 | 0.1308 | 0.7129 | 0.0024 | 0.0005 |
| miR-30f-5p | 0.3125 | 0.03677 | 0.3667 | 0.0753 | 0.05764 | 0.03747 | 0.0936 | 0.0145 | 0.0306 | 0.0005 |
| miR-30f | 0.1714 | 0.02009 | 0.1513 | 0.0292 | 0.01949 | 0.0217 | 0.0341 | 0.0061 | 0.021 | 0.0005 |
| miR-4791 | 0.0018 | 0.00638 | 0 | 0.0097 | 0.01338 | 0.01318 | 0.0005 | 0.135 | 0.0006 | 0.0005 |
| miR-19a | 0.0008 | 0.00642 | 0 | 0.0023 | 0.00332 | 0.00626 | 0.0007 | 0.0061 | 0.0046 | 0.0005 |
| miR-363-3p | 0.0043 | 0.01035 | 0.0018 | 0.0094 | 0.0035 | 0.00295 | 0.0014 | 0.0024 | 0.0006 | 0.0005 |
| miR-15a-5p | 0.0005 | 0.00793 | 0 | 0.0006 | 0.00101 | 0.00905 | 0 | 0.0011 | 0.0018 | 0.0005 |
| miR-500a-3p | 0.0085 | 0.00177 | 0.0081 | 0.0082 | 0.00808 | 0.0022 | 0.0128 | 0.0044 | 0.0021 | 0.0005 |
| miR-2285aa | 0.0012 | 0.00098 | 0.0014 | 0.0059 | 0.00529 | 0.00161 | 0.0031 | 0.0145 | 0.0005 | 0.0005 |
| miR-150 | 0.0016 | 0.00151 | 0.0003 | 0.0013 | 0.00194 | 0.00065 | 1E−04 | 0 | 0.0002 | 0.0005 |
| miR-148b-5p | 0.0005 | 0.0006 | 0.0009 | 0.0023 | 0.00253 | 0.00122 | 0.0017 | 0.0046 | 0.0008 | 0.0005 |
| miR-196a | 0.0022 | 0.00053 | 0.0036 | 0.0015 | 0.00026 | 9.2E−05 | 0.0002 | 0.0007 | 0.0006 | 0.0005 |
| miR-486 | 0.0023 | 0.00019 | 0.0026 | 0.0005 | 0.00414 | 0.00041 | 0.0007 | 0.0002 | 0.0002 | 0.0005 |
| miR-30d-5p | 0.0006 | 0.00026 | 0.0007 | 0 | 0.0006 | 0.00011 | 0.0009 | 0.0002 | 0.0004 | 0.0005 |
| miR-2284x | 0.1734 | 0.21952 | 0.0675 | 0.2153 | 0.08789 | 0.07918 | 0.0572 | 0.1392 | 0.0391 | 0 |
| miR-2285t | 0.0882 | 0.56778 | 0.1192 | 0.305 | 0.00011 | 9.2E−05 | 0.0002 | 0 | 0.023 | 0 |
| miR-3431-5p | 0.0004 | 0.00019 | 0 | 0.0015 | 0.13193 | 0.09277 | 0.1542 | 0.078 | 0 | 0 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-2284y | 0.0643 | 0.06373 | 0.026 | 0.1059 | 0.02966 | 0.02109 | 0.0223 | 0.0493 | 0.0084 | 0 |
| miR-340-5p | 0.0289 | 0.15978 | 0.0463 | 0.0208 | 0.01617 | 0.0609 | 0.0106 | 0.0761 | 0.0106 | 0 |
| miR-6529a | 0.027 | 0.00615 | 0.0198 | 0.0374 | 0.03752 | 0.01171 | 0.0867 | 0.1131 | 0.0019 | 0 |
| miR-4693-3p | 0 | 0 | 0 | 0.0003 | 0.00011 | 0 | 0.0009 | 0.3289 | 0 | 0 |
| miR-379-5p | 0.0008 | 0.00113 | 0.0007 | 0.0016 | 0.04806 | 0.02497 | 0.0793 | 0.0731 | 0.0002 | 0 |
| miR-345-3p | 0.0231 | 0.01295 | 0.013 | 0.0152 | 0.02545 | 0.02136 | 0.0194 | 0.0234 | 0.0055 | 0 |
| miR-7154-3p | 0 | 0 | 0 | 0 | 0 | 0 | 0 | 0.178 | 0 | 0 |
| miR-140-5p | 0.0038 | 0.0085 | 0.0049 | 0.0122 | 0.02034 | 0.01235 | 0.0023 | 0.0302 | 0.0013 | 0 |
| miR-3432-5p | 0.0039 | 0.00038 | 0.0039 | 0.0013 | 0.04616 | 0.00556 | 0.0844 | 0.0247 | 0.0004 | 0 |
| miR-411a | 0.0008 | 0.00015 | 0.0014 | 0.001 | 0.0367 | 0.01551 | 0.0339 | 0.0696 | 0.0001 | 0 |
| miR-429 | 0.004 | 0.00449 | 0.004 | 0.006 | 0.01364 | 0.01248 | 0.0116 | 0.0188 | 0.0004 | 0 |
| miR-3431-3p | 0 | 0.00019 | 0 | 0.0005 | 0.03361 | 0.03335 | 0.0321 | 0.012 | 0 | 0 |
| miR-142-3p | 0 | 0.00917 | 0 | 0.0393 | 0.00395 | 0.00746 | 0.0024 | 0.1243 | 0.0002 | 0 |
| miR-3432a | 0.0287 | 0.00264 | 0.1067 | 0.0226 | 0.00056 | 0.00048 | 0.0013 | 0.0002 | 0.0033 | 0 |
| miR-142-5p | 0.0003 | 0.00468 | 0 | 0.0032 | 0.00231 | 0.00886 | 0.0011 | 0.0412 | 0 | 0 |
| miR-429 | 0.0216 | 0.00948 | 0.0156 | 0.0146 | 0.01297 | 0.00709 | 0.0093 | 0.0145 | 0.0013 | 0 |
| miR-718 | 0 | 0 | 3.0593 | 0.0012 | 0.00156 | 0.00015 | 0.0087 | 0 | 0 | 0 |
| miR-382-5p | 0.0014 | 0.00042 | 0.002 | 0.0013 | 0.01229 | 0.00565 | 0.0307 | 0.0059 | 0 | 0 |
| miR-769 | 0.0115 | 0.00642 | 0.007 | 0.0167 | 0.02489 | 0.00861 | 0.0197 | 0.0628 | 0.0025 | 0 |
| miR-381 | 0.0001 | 0.00019 | 0 | 0.0004 | 0.01315 | 0.025 | 0.0135 | 0.0108 | 0.0005 | 0 |
| let-7a-3p | 0.0049 | 0.01423 | 0.0065 | 0.0009 | 0.00402 | 0.01422 | 0.0019 | 0.0036 | 0.0068 | 0 |
| miR-493-5p | 0.0002 | 7.6E−05 | 0 | 0 | 0.00768 | 0.01734 | 0.0025 | 0.0048 | 0.0004 | 0 |
| miR-362-5p | 0.0179 | 0.00242 | 0.0147 | 0.0138 | 0.0063 | 0.00231 | 0.0111 | 0.0085 | 0.0009 | 0 |
| miR-342 | 0.004 | 0.00453 | 0.0027 | 0.013 | 0.0076 | 0.00923 | 0.0075 | 0.0042 | 0.0009 | 0 |
| miR-885-3p | 0.0049 | 0.00102 | 0.0087 | 0.0022 | 0.00592 | 0.00353 | 0.0167 | 0.0055 | 0.0006 | 0 |
| miR-493-3p | 0.0001 | 0 | 0.0004 | 0.0002 | 0.00898 | 0.01012 | 0.0127 | 0.016 | 0 | 0 |
| miR-374a-3p | 0.0019 | 0.00623 | 0.003 | 0.0008 | 0.0019 | 0.00519 | 0.0009 | 0.0065 | 0.0003 | 0 |
| miR-146b-3p | 0.0007 | 0 | 0.0005 | 0.0006 | 0.01382 | 0.00325 | 0.0294 | 0.0058 | 0 | 0 |
| miR-1777b | 0 | 0 | 1.1732 | 0.0015 | 0.00015 | 0 | 0.0064 | 0.0004 | 0 | 0 |
| miR-409-3p | 0.0001 | 0 | 0.0008 | 0 | 0.00402 | 0.00722 | 0.0182 | 0.0037 | 0.0001 | 0 |
| miR-7113-5p | 0 | 0 | 0 | 0.0003 | 0 | 0 | 0.0002 | 0.1158 | 0 | 0 |
| miR-374a | 0.0031 | 0.00268 | 0.0033 | 0.001 | 0.00391 | 0.00332 | 0.0014 | 0.0086 | 0.0018 | 0 |
| miR-2419-5p | 0.0218 | 0.00298 | 0.0114 | 0.0056 | 0 | 0 | 0 | 0 | 0.0016 | 0 |
| miR-3958-3p | 0.0002 | 0 | 0 | 0.0002 | 0.00596 | 0.0031 | 0.0034 | 0.0043 | 0 | 0 |
| miR-2285f | 0.0005 | 0.00378 | 0.0004 | 0.0102 | 0.0041 | 0.0014 | 0.0015 | 0.0139 | 0 | 0 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-345-5p | 0.0009 | 0.002 | 0 | 0.0029 | 0.00473 | 0.00174 | 0.002 | 0.0037 | 0.0005 | 0 |
| miR-136-3p | 0 | 0.00015 | 0 | 0.0002 | 0.00216 | 0.00683 | 0.001 | 0.0036 | 0 | 0 |
| miR-1468-5p | 0.0109 | 0.00079 | 0.0263 | 0.0034 | 0.00145 | 0.00046 | 0.0032 | 0 | 0.0017 | 0 |
| miR-1273g-3p | 0.0085 | 0.00045 | 0.0326 | 0.0032 | 0.00089 | 0.00015 | 0.0022 | 0.0011 | 0.0012 | 0 |
| miR-30f-3p | 0 | 0 | 0 | 0 | 0.00343 | 0.00057 | 0.01 | 0.0035 | 0 | 0 |
| let-7f-3p | 0.001 | 0.00042 | 0.0003 | 0.0002 | 0.00205 | 0.00552 | 0.0007 | 0.0015 | 0.0006 | 0 |
| miR-708-3p | 0 | 0.00053 | 0 | 0.0007 | 0.00455 | 0.0065 | 0.0032 | 0.0058 | 0 | 0 |
| miR-380-3p | 0 | 0 | 0 | 0 | 0.00265 | 0.00454 | 0.0005 | 0.0011 | 0 | 0 |
| miR-1271 | 0 | 7.6E−05 | 0 | 0.0004 | 0.00533 | 0.00142 | 0.0077 | 0.0041 | 0 | 0 |
| miR-664b | 0.0194 | 0.00461 | 0.0157 | 0.0013 | 0.01021 | 0.00489 | 0.0046 | 0.0044 | 0.0034 | 0 |
| miR-1469 | 0 | 0 | 0.184 | 0.0008 | 0 | 0 | 0.0002 | 0 | 0 | 0 |
| miR-2284ab | 0.0023 | 0.00536 | 0.001 | 0.0071 | 0.00153 | 0.00174 | 0.0021 | 0.0029 | 0 | 0 |
| miR-1343 | 0.0075 | 0.00064 | 0.0059 | 0.0005 | 0.00387 | 0.00153 | 0.0025 | 0.0011 | 0.0006 | 0 |
| miR-20b | 0.0023 | 0.00094 | 0.0014 | 0.0039 | 0.00253 | 0.00052 | 0.0015 | 0.0013 | 0 | 0 |
| miR-340-3p | 0.0028 | 0.00023 | 0.0046 | 0.0003 | 0.00134 | 0.00072 | 0.0017 | 0.0002 | 0.0005 | 0 |
| miR-2285ae | 0 | 0 | 0 | 0 | 0.00078 | 0.00336 | 0.0003 | 0.0038 | 0 | 0 |
| miR-96 | 0.001 | 0.002 | 0.0012 | 0.0034 | 0.00034 | 0.00055 | 0.0003 | 0.0011 | 0.0008 | 0 |
| miR-2463 | 0.0004 | 0.00249 | 0 | 0.0141 | 0.00406 | 0.00109 | 0.006 | 0.0065 | 0 | 0 |
| miR-411a-5p | 0 | 0.00011 | 0 | 0.0001 | 0.00339 | 0.00508 | 0.0053 | 0.008 | 0 | 0 |
| miR-204-5p | 0 | 0.00011 | 0 | 0.0003 | 0.00451 | 0.0009 | 0.0024 | 0.0006 | 0 | 0 |
| miR-500-5p | 0.0066 | 0.00193 | 0.0036 | 0.0041 | 0.00291 | 0.001 | 0.0029 | 0.0013 | 0.0005 | 0 |
| miR-2885 | 0.0223 | 0.0031 | 0.0356 | 0.0203 | 0 | 0 | 0 | 0 | 0.0005 | 0 |
| miR-29b-3p | 0.0027 | 0.00563 | 0.0012 | 0.0019 | 0.00026 | 0.00144 | 0.0007 | 0.0012 | 0.0012 | 0 |
| miR-125a-5p | 0.0044 | 0 | 0.0059 | 0.0002 | 0.00026 | 0.00011 | 0 | 0 | 0.0002 | 0 |
| miR-32 | 0.0023 | 0.01454 | 0.0056 | 0.0039 | 0 | 0 | 0 | 0 | 0.0001 | 0 |
| miR-32-5p | 0 | 0 | 0 | 0 | 0.00201 | 0.00412 | 0.0008 | 0.0083 | 0.0011 | 0 |
| miR-451 | 0.0001 | 0.00026 | 0 | 0.0004 | 0.00402 | 0.00153 | 0 | 0.0002 | 0 | 0 |
| miR-106a-5p | 0.0008 | 0.00102 | 0.0009 | 0.0037 | 0.00063 | 0.00041 | 0.0009 | 0.001 | 0.0002 | 0 |
| miR-323b | 0 | 0 | 0 | 0 | 0.00138 | 0.00229 | 0.0017 | 0.0007 | 0 | 0 |
| miR-6741-5p | 0 | 0.00106 | 0 | 0.0075 | 0.0006 | 0.00486 | 0.001 | 0.0017 | 0 | 0 |
| miR-6119-5p | 0.0002 | 0.0014 | 0.001 | 0.0022 | 0.00123 | 0.00159 | 0.001 | 0.0088 | 0 | 0 |
| miR-126-3p | 0.0002 | 0.0003 | 0.0005 | 0.0052 | 0.00052 | 3.7E−05 | 0.0008 | 0.0034 | 0 | 0 |
| miR-374a-5p | 0.0001 | 0.00083 | 0.0007 | 0.0002 | 0.00052 | 0.0017 | 0.0004 | 0.0033 | 0.0001 | 0 |
| miR-15b-3p | 0.0005 | 0.00045 | 0 | 0 | 0.00123 | 0.00183 | 1E−04 | 0.0011 | 0.0016 | 0 |
| miR-136-3p | 0 | 0 | 0 | 0 | 0.00104 | 0.00247 | 0.0004 | 0.0014 | 0 | 0 |
| miR-146a | 0 | 7.6E−05 | 0 | 0 | 0.00101 | 0.00222 | 0.0007 | 0.0002 | 0.0011 | 0 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-323a-3p | 0.0003 | 7.6E−05 | 0 | 0 | 0.00145 | 0.00229 | 0.0006 | 0 | 0 | 0 |
| miR-376c-3p | 0 | 0 | 0 | 0 | 0.00048 | 0.0026 | 0.0002 | 0.0016 | 0 | 0 |
| miR-410-3p | 0 | 0 | 0 | 0 | 0.00078 | 0.00251 | 0.0006 | 0.0007 | 0 | 0 |
| miR-331-3p | 0.0059 | 0.00128 | 0.0047 | 0.0014 | 0.00205 | 0.00153 | 0.0011 | 0 | 0.0008 | 0 |
| miR-370 | 0 | 0 | 0 | 0.0001 | 0.00093 | 0.0007 | 0.0049 | 0.0007 | 0 | 0 |
| miR-2387 | 0.0027 | 0.00011 | 0.0035 | 0.0012 | 0 | 0 | 0.0004 | 0 | 0.0002 | 0 |
| miR-708-5p | 0 | 7.6E−05 | 0 | 0.0001 | 0.00209 | 0.00087 | 0.002 | 0.0018 | 0 | 0 |
| miR-655 | 0 | 0 | 0 | 0 | 0.00108 | 0.00235 | 0.0003 | 0.0003 | 0 | 0 |
| miR-2285k | 0.0014 | 0.0057 | 0.0012 | 0.0123 | 7.5E−05 | 3.7E−05 | 1E−04 | 0.0002 | 0.0002 | 0 |
| miR-2284j | 0.002 | 0.01193 | 0.0034 | 0.0042 | 0 | 0 | 0 | 0 | 0.0003 | 0 |
| miR-1296 | 0 | 0 | 0 | 0 | 0.00194 | 0.00035 | 0.0038 | 0.001 | 0 | 0 |
| miR-6120-3p | 0.0025 | 0.00215 | 0.0018 | 0.0017 | 0 | 0 | 0 | 0 | 0.0001 | 0 |
| miR-4454 | 0.0016 | 0.00015 | 0.0004 | 0.0006 | 0.00287 | 0.00144 | 0.0035 | 0.0016 | 0.0003 | 0 |
| let-7b-3p | 0.0012 | 0.00023 | 0.0007 | 0.0002 | 0.00045 | 0.00138 | 0.0005 | 0.0002 | 0.0004 | 0 |
| miR-127 | 0 | 0 | 0 | 0 | 0.00052 | 0.00114 | 0.0036 | 0 | 0 | 0 |
| miR-2285ad | 0 | 0 | 0 | 0 | 0.00156 | 0.00065 | 0.0032 | 0.0003 | 0 | 0 |
| miR-6524 | 0.0021 | 0.0054 | 0.0009 | 0.0018 | 0 | 0 | 0 | 0 | 0.0004 | 0 |
| miR-2285p | 0 | 0.00302 | 0.0003 | 0.0032 | 0 | 0 | 0 | 0 | 0.0001 | 0 |
| miR-3976 | 0 | 0 | 0 | 0 | 0.0041 | 0.00103 | 0.0005 | 0.0071 | 0 | 0 |
| miR-10b-5p | 0.0008 | 0.00023 | 0.0004 | 0.0002 | 0.00104 | 0.00432 | 0.0002 | 0.0007 | 0.0015 | 0 |
| miR-107 | 0.0007 | 0.00011 | 0 | 0.0013 | 0.00082 | 0.00076 | 0.0007 | 0.0014 | 0.0003 | 0 |
| miR-215 | 0.0008 | 0.00121 | 0.0023 | 0.0015 | 0.00026 | 0.00013 | 0.0003 | 0.0002 | 0.0004 | 0 |
| miR-432-5p | 0.0003 | 0 | 0.0003 | 0.0003 | 0.00164 | 0.00068 | 0.0065 | 0.0007 | 0 | 0 |
| miR-2887 | 0.0012 | 0.00011 | 0.0872 | 0.001 | 0.00056 | 0.00018 | 0.0016 | 0.0003 | 0.0003 | 0 |
| miR-762 | 0.0034 | 0.00136 | 0.0007 | 0.0015 | 0 | 0 | 0 | 0 | 0.0004 | 0 |
| miR-139 | 0.0003 | 0.00045 | 0.0005 | 0.0026 | 0.00063 | 0.00037 | 0.0009 | 0.0002 | 0.0001 | 0 |
| miR-1388-5p | 0.0003 | 0.0006 | 0 | 0.0014 | 0.00078 | 0.00041 | 0.0008 | 0.0021 | 0 | 0 |
| miR-1271-5p | 0.0003 | 0.00015 | 0.0003 | 0.0004 | 0.00078 | 0.00081 | 0.0012 | 0.0015 | 0 | 0 |
| miR-2285x | 0 | 0.00015 | 0 | 0.0002 | 0.00138 | 0.0012 | 0.0002 | 0.0133 | 0 | 0 |
| miR-3178 | 0 | 0 | 0 | 0 | 0.00019 | 0 | 0.0055 | 0.0008 | 0 | 0 |
| miR-2285e | 0.0014 | 0.00162 | 0.0013 | 0.0024 | 0.00034 | 5.5E−05 | 0 | 0.0045 | 0.0002 | 0 |
| miR-3959-5p | 0 | 0 | 0.0003 | 0 | 0.00101 | 0.00065 | 0.0011 | 0.0029 | 0 | 0 |
| miR-2419-3p | 0.0027 | 0.00011 | 0.0075 | 0.0029 | 0 | 0 | 0 | 0 | 0.0001 | 0 |
| miR-7-1-3p | 0.0007 | 0.00094 | 0.0007 | 0.0013 | 0.00197 | 0.0012 | 0.0009 | 0.0016 | 0.0004 | 0 |
| miR-330 | 0.0007 | 7.6E−05 | 0.0004 | 0.0007 | 0.00075 | 0.00028 | 0.0016 | 0.0013 | 0.0003 | 0 |

TABLE 1-continued percentage of the indicated miRNA identified (out of total miRNA reads) in different milk fractions (skim (S) or fat (F)) of milk from various sources (cow, goat and human), pasteurized (P) or not pasteurized (NP)

| miRNA Identity | % of miRNA in cow S/NP | % of miRNA in cow F/NP | % of miRNA in cow S/P | % of miRNA in cow F/P | % of miRNA in goat S/NP | % of miRNA in goat F/NP | % of miRNA in goat S/P | % of miRNA in goat F/P | % of miRNA human S | % of miRNA human F |
|---|---|---|---|---|---|---|---|---|---|---|
| miR-340 | 0.0015 | 7.6E-05 | 0.0025 | 0 | 0.00071 | 0.00028 | 0.0005 | 0.0002 | 0.0002 | 0 |
| miR-323 | 0.0001 | 0 | 0.0003 | 0 | 0.00078 | 0.00126 | 0.0008 | 0.0003 | 0 | 0 |
| miR-296-3p | 0.0003 | 0.00015 | 0.0003 | 0.0013 | 0.00063 | 5.5E-05 | 0.0013 | 0.0022 | 0 | 0 |
| miR-324-5p | 0 | 0.00023 | 0 | 0.0004 | 0.00086 | 0.00061 | 0.0002 | 0.0026 | 0.0001 | 0 |
| miR-485 | 0 | 0 | 0.0003 | 0 | 0.00119 | 0.00031 | 0.0023 | 0.0003 | 0 | 0 |
| miR-1249-5p | 0 | 0 | 0.0111 | 0.0006 | 0 | 0 | 0.0003 | 0 | 0 | 0 |
| miR-2285b | 0 | 0.00113 | 0 | 0.0012 | 0.00034 | 0.00028 | 1E-04 | 0.0018 | 0 | 0 |
| miR-141-5p | 0.0003 | 0.00057 | 0.0008 | 0.0006 | 0.00015 | 0.00052 | 0.0005 | 0.0011 | 0 | 0 |
| miR-532-3p | 0.001 | 0.0006 | 0.001 | 0.0004 | 0.00078 | 0.00018 | 0.0003 | 0 | 0.0002 | 0 |
| let-7f-2-3p | 0.0001 | 0.00064 | 0 | 0.0001 | 0.00056 | 0.00087 | 0.0002 | 0.0002 | 0.0003 | 0 |
| miR-7862 | 0.0003 | 0.00015 | 0.0004 | 0.0005 | 0.0013 | 0.00022 | 0.0008 | 0.0006 | 0 | 0 |
| miR-6517 | 0.0019 | 0 | 0.0035 | 0.0006 | 0 | 0 | 0 | 0 | 0 | 0 |
| miR-495-3p | 0 | 0 | 0 | 0 | 0.00071 | 0.00127 | 0.0001 | 0.0004 | 0 | 0 |
| miR-99a-3p | 0.0007 | 0.00053 | 0.0003 | 0.0008 | 0.00015 | 0.00048 | 0.0006 | 0.0002 | 0.0004 | 0 |
| miR-215-5p | 0.0002 | 0.00185 | 0.0003 | 0.0007 | 0.00011 | 0.00018 | 0 | 0 | 0.0002 | 0 |
| miR-299-3p | 0.0001 | 0 | 0 | 0 | 0.00063 | 0.00017 | 0.003 | 0.0002 | 0 | 0 |
| miR-6729-5p | 0.0002 | 0 | 0.0007 | 0.0006 | 0.00067 | 0 | 0.0019 | 0.0008 | 0 | 0 |
| miR-204-3p | 0 | 0 | 0 | 0.0001 | 0.00052 | 0.00018 | 0.0025 | 0.0014 | 0 | 0 |
| miR-2890 | 0 | 0 | 0.0118 | 0 | 0 | 0 | 1E-04 | 0 | 0 | 0 |
| miR-409-3p | 0 | 0 | 0 | 0 | 0.00071 | 0.00105 | 0.0042 | 0.0011 | 0 | 0 |
| miR-505-3p | 0.0005 | 0.00034 | 0.0004 | 0.0001 | 0.00056 | 0.00057 | 1E-04 | 0.0004 | 0.0002 | 0 |
| miR-2484 | 0.0001 | 0.00261 | 0 | 0.0008 | 0 | 0 | 0 | 0 | 0 | 0 |
| miR-342-5p | 0.0001 | 0 | 0.0014 | 0.0004 | 0.00019 | 5.5E-05 | 0.0023 | 0.0005 | 0 | 0 |
| miR-6522 | 0.001 | 0.00185 | 0.0003 | 0.0005 | 0 | 0 | 0 | 0 | 0.0003 | 0 |
| miR-2336 | 0.0008 | 0.00155 | 0.0007 | 0.0012 | 0 | 0 | 0 | 0 | 0 | 0 |
| miR-519d-5p | 0.0004 | 0 | 0.0005 | 0.0019 | 0.00022 | 0 | 0.0008 | 0.0007 | 0 | 0 |
| miR-1291 | 0 | 0 | 0 | 0 | 0 | 0 | 0 | 0.0066 | 0 | 0 |
| miR-411a-3p | 0 | 0 | 0 | 0 | 0.00086 | 0.00066 | 0.0007 | 0.0007 | 0 | 0 |
| miR-382-3p | 0 | 0 | 0 | 0 | 0.00026 | 0.00102 | 0.0003 | 0.0007 | 0 | 0 |
| miR-221-5p | 0 | 0.0003 | 0 | 0 | 0.00134 | 0.00048 | 0 | 0.0006 | 0 | 0 |
| miR-9-3p | 0.0001 | 0.00023 | 0 | 0 | 0.00037 | 0.00089 | 0 | 0.0005 | 0.0003 | 0 |
| miR-487b-3p | 0 | 0 | 0 | 0 | 0.00071 | 0.00076 | 0.0002 | 0.0008 | 0 | 0 |
| miR-502b-5p | 0.0009 | 0.00011 | 0.0018 | 0.0001 | 0.00067 | 9.2E-05 | 0.0003 | 0.0002 | 0 | 0 |
| miR-369-5p | 0 | 0 | 0 | 0 | 0.00112 | 0.00033 | 0.001 | 0.0003 | 0 | 0 |

Example 2

Validation of the Next Generation Sequencing (NGS) Results by RealTime PCR (qRT-PCR).

A. Expression of miRNA-148a-3p in breast milk—Milk samples were collected from human mothers from pre-term and term babies at different times of lactation. Preterm mothers were mothers to babies born at weeks 28-36 of pregnancy. Term mothers were mothers to babies born at weeks 37-42 to pregnancy. Milk samples were collected on 2 days postpartum-colostrum, 1 month postpartum, 3 month postpartum, 6 month postpartum and 9 months postpartum. NGS analysis revealed that miRNA-148a-3p (mir-148a) is one of the predominantly expressed miRNAs in the skim and fat fraction of the breast milk from mothers of pre-term and term infants. This result was validated by qRT-PCR in breast milk of different mothers at one month of lactation. It was found that mir-148a is highly expressed, compared to others miRNAs (such as miRNA-146a), in the milk of most of the mothers that were analyzed. It was also found that the levels of mir-148a are variable in the different fractions of the milk (FIGS. 5A-D).

Figure 6:
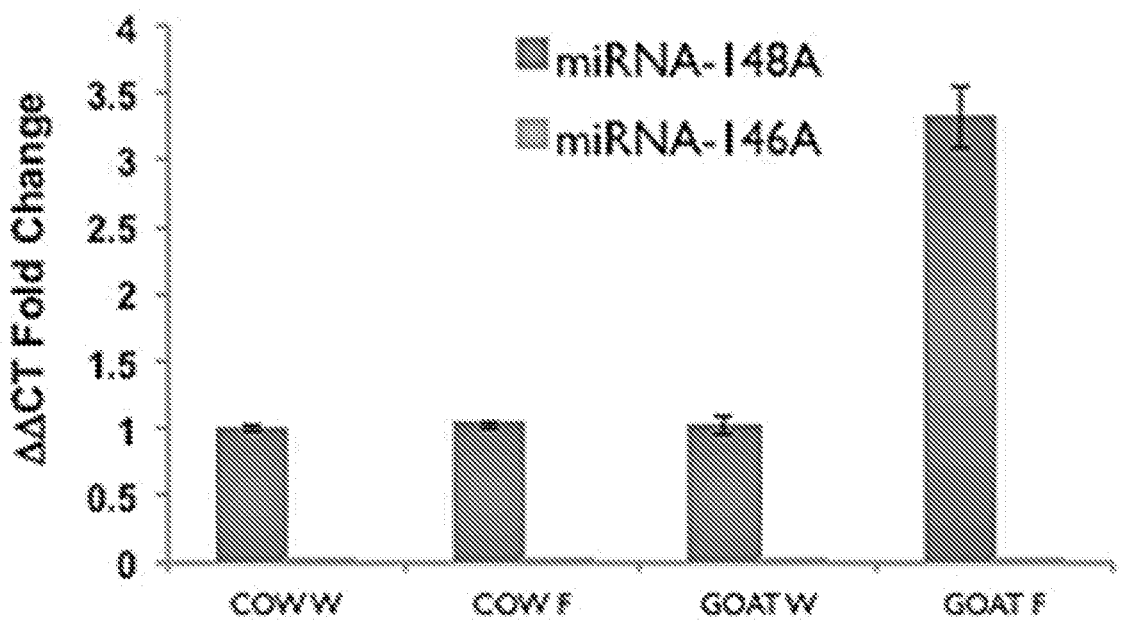
FIG. 6—Bar graphs showing the expression of the miRNA-148a and miRNA-146a in the fat and skim fraction cow and goat milk. Total RNA from the fat (F) and skim (W) fraction of cow and goat milk was isolated and the expression of the mir-148a and miRNA 146a were analyzed by qRT-PCR. The qRT-PCR results were calculated by Delta-Delta CT Method ($\Delta\Delta$Ct), values were normalized against RNU6B.

B. Expression of miRNA-148a-3p in cow and goat milk—Milk samples were collected from goat and cow. NGS analysis identified that miRNA-148a-3p is one of the predominantly expressed miRNAs in the skim and fat fraction of the cow and goat milk This result was validated by qRT-PCR (FIG. 6). It was found that the mir-148a is highly expressed, compared to others miRNAs (such miRNA-146a), in the milk of cow and goat (FIG. 6).

Example 3

Expression of miRNA in Milk Based Infant Formulas

Figure 7:
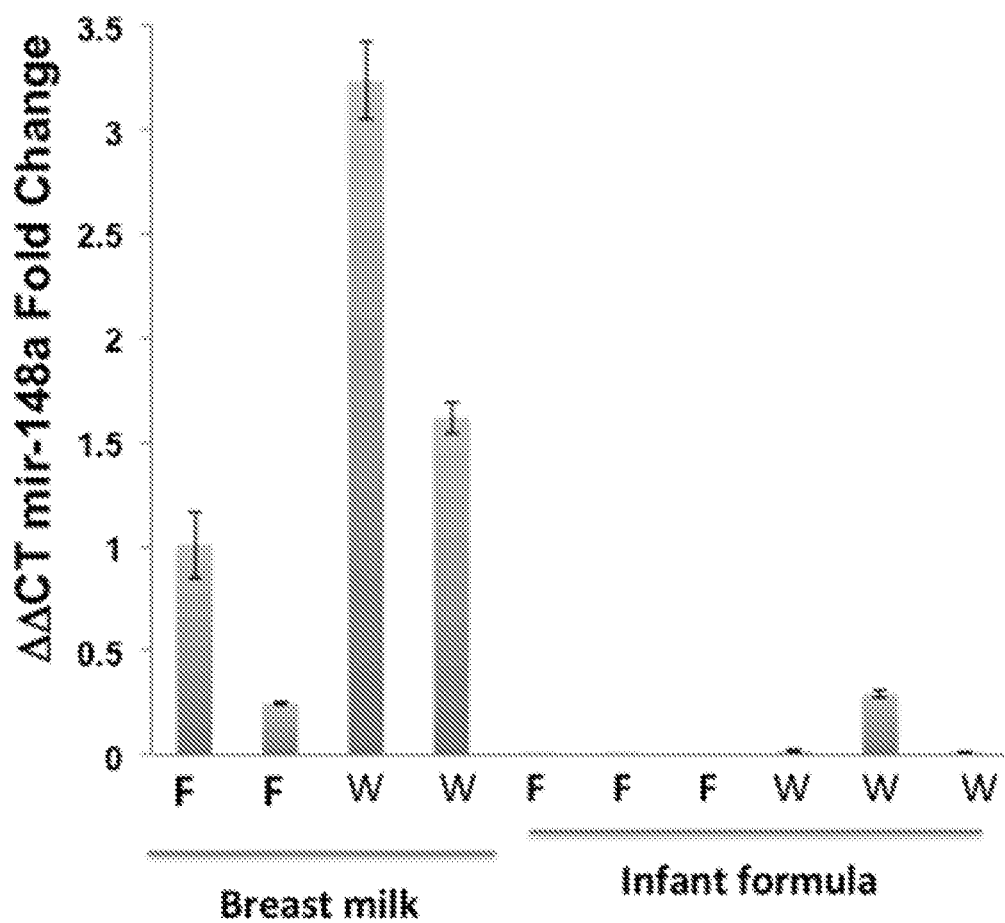
FIG. 7. Expression of miRNA-148a-3p in the skim and fat fraction of human milk from term and infant milk-formula. Total RNA from the skim (W) and fat fraction (F) of the breast milk and three different types of cow based infant formula were isolated and expression of miRNA-148a-3p was analyzed by qRT-PCR. The qRT-PCR results were calculated by Delta-Delta CT method ($\Delta\Delta$Ct), values were normalized against RNU6B.

The expression of miRNA 148a-3p was analyzed in three different commercial milk-based infant formulas (including, "Materna-extracare Stage I", "Similac Advance+" and Nutrilon). Total RNA was isolated from the fat (F) and skim fractions (W). As shown in the bar graphs in FIG. 7, the expression of miRNA 148a-3p, milk, was significantly lower in the infant formula than the miRNA level in cow, goat, or human milk These results indicate that the commercial milk formulas lack essential components, which are present in natural milk

Example 4

Effect of Exosomes and Fat Globules Isolated from Breast Milk on Normal and Cancer Cells The miRNAs that were found in the skim fraction of the breast milk are encapsulated by exosomes (milk exosomes). Using the Exoquick reagent (SBI , EXOQ20A-1) exosomes were isolated from breast milk Alternatively, exosomes were isolated by centrifugation (as detailed below in Example 6). Following isolation, the Exo-Red kit (SBI , EXOR100A-1) which binds to fluorescently-label single-stranded RNAs inside the isolated exosomes was used.

The lipid fraction of the milk was likewise labeled using the Exo-Red kit.

The exosomes isolated from breast milk and lipid fraction of the breast milk at one month of lactation, were labeled and then incubated with CRL 1831 cells (normal intestine cell line), K562 (leukemia cells) and Lim1215 cancer cells. Two hours after incubation of the cells with the labeled exosomes and/or fat globules, cells were visualized by fluorescent microscopy. The results presented in FIG. 8A show that all the normal cells (left panel) and cancer cells (middle and right hand panel) were positively labeled, which indicate that the exosomes and fat globules were taken into the cells.

The RNA content of the lipid fraction of the milk was also labeled and then incubated with CRL 1831 cells. Cells incubated with the fat layer of the milk visualized by fluorescent microscopy were positively labeled, which indicates that the RNA content of the fat layer was also taken into the cells (FIG. 8C). The RNA content from the skim and fat layers from the human milk enters the cells and the expression of miRNA-148a was found to be up-regulated compared to control cells (FIG. 8B, 8D).

Total RNA was isolated from the cells that were incubated with milk exosomes and lipid fraction globules and the expression of miRNA-148a was analyzed by qRT-PCR. Thus, the results presented indicate that incubation of the cells with milk exosomes, and/or the lipid fraction of the milk, exhibit elevated presence (level) of miRNA-148a as compared to control cells.

miRNAs are known to regulate gene expression post-transcriptionally by either inhibiting protein translation or degrading target mRNAs. For example, DNMT1 is a target gene of mir-148a. As shown in FIGS. 9A-D, the expression of DNTM1, a target gene of mir-148a, was found to be down-regulated in cells with up-regulation of mir-148a after incubation with milk-derived miRNA from the skim and fat layers.

Example 5

Effect of Exosomes and Fat Globules Isolated from Breast Milk on the miRNA Expression in the Intestine (Ex-Vivo)

As in Example 3, the exosomes isolated from breast milk and fat globules isolated from fat fraction of the breast milk at one month of lactation, were labeled and then incubated with a section of intestine isolated from mice (ex-vivo). One day after incubation of the intestine section with the labeled exosomes and fat globules, cells were visualized by fluorescent microscopy. The intestine sections were positively labeled, which indicate that the exosomes and fat globules were taken into the intestine (FIG. 10A). Total RNA was isolated from the intestine incubated with milk exosomes and/or fat globules, and the expression of miRNA-148a was analyzed by qRT-PCR. The results presented in FIG. 10B indicated that the expression of miRNA-148a was elevated compared to control sections (FIG. 10B).

Example 6

Isolation of Microvesicles from Milk by Centrifugation

Provided is an advantageous preparation method of microvesicles from milk, which does not involve use of columns or other separation reagents, other than commonly used, inert buffers. This preparation method is both safe since only centrifugation steps are used for isolation and only buffer is for washing at the last steep of exosomes isolation. Further, this preparation method is both cost and time efficient.

Figure 11A:
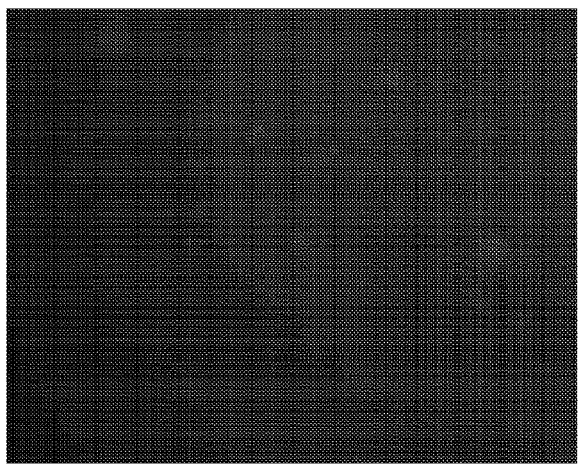
FIGS. 11A-11B—Microvesicles isolated from milk conatin miRNA—The fat layer of milk, obtained after centrifugation of the milk was stained by acridine red (FIG. 11A). The stained RNA located in the fat globules of the fat layer of milk was visualized by fluorescent microscope analysis (FIG. 11B). The identity of the milk derived miRNA in the fat layer was detected by qRT-PCR.
Figure 11B:
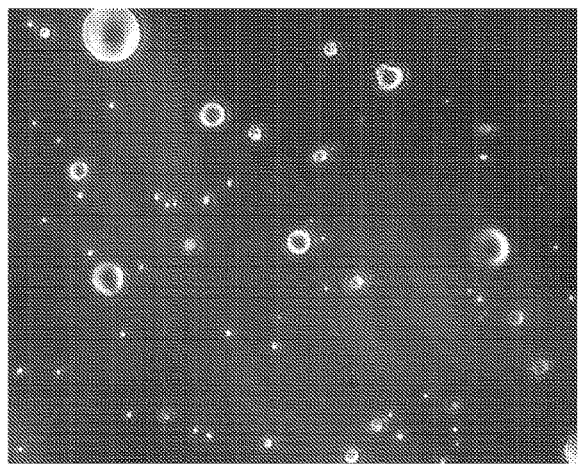

The exemplary isolation method include sequential centrifugations of fractions of milk An initial volume of 40 ml of cow milk is used and centrifuged at 4000 g for one hour at 4° C. to obtain the two layer of milk: fat layer and skim milk. In order to show that the obtained fat layer (which include fat globules (FIG. 11B)) indeed contain miRNA, the fat layer was stained by acridine red. The stained RNA in the fat globules was visualized by fluorescent microscope analysis (FIG. 11A-B). Milk derived miRNA in the fat layer was further detected by qRT-PCR.

The skim layer of the milk (supernatant) was then centrifuged at 10000 g for 30 minutes at 4° C. The pellet (cells debris) was discard and the supernatant (sup) is kept for the next steps. The supernatant is then centrifuged at 100000 g 70 minutes at 4° C. The pellet is washed with PBS buffer and centrifuged again at 100000 g for 70 minutes at 4° C. The resulting pellet, which includes exosomes is kept for further use milk miRNAs was further detected in the exosomes isolated by this ultra-centrifugation procedure.

The fat globules and/or exosomes thus obtained can be readily added to supplement milk formulas. Alternatively, the fat globules and/or exosomes thus obtained may be dehydrated and added to milk formulas in dehydrated form.

The invention claimed is:

1. A composition comprising infant formula and microvesicles isolated from skim fraction of natural milk, wherein the microvesicles encapsulate or comprise miRNA molecules, wherein the miRNA molecules comprise miR-148a and miR-6073, wherein the microvesicles further encapsulate or comprise biologically active compounds, and wherein the composition substantially does not include cells present in natural milk.

2. The composition of claim 1, wherein the natural milk is obtained from bovine, goat or human.

3. The composition of claim 1, wherein the microvesicles comprise exosomes.

4. The composition of claim 1, wherein the biologically active compounds are selected from nucleic acid molecules, lipids, proteins and peptides.

5. The composition of claim 1, wherein the infant formula is devoid of animal derived fat other than the fat originating from the microvesicles.

6. The composition of claim 1, wherein the infant formula does not comprise miRNA molecules other than miRNA molecules comprised within the microvesicles.

7. The composition of claim 1, wherein the microvesicles are in hydrated or lyophilized form.

8. The composition of claim 1, wherein the infant formula is formulated for oral administration to infants.

9. The composition of claim 1, wherein the natural milk is pasteurized.

10. The composition of claim 1, wherein the natural milk is not pasteurized.

11. A method for enriching an infant formula, the method comprising adding an effective amount of microvesicles isolated from skim fraction of natural milk to the infant formula, thereby obtaining an enriched infant formula composition, wherein the infant formula is devoid of animal derived fat, wherein the microvesicles encapsulate or comprise miRNA molecules, wherein the miRNA molecules comprise miR-148a and miR-6073, wherein the microvesicles further encapsulate or comprise biologically active compounds, and wherein the enriched infant formula composition substantially does not include cells present in natural milk.

12. A method of treating cancer in a subject in need thereof, the method comprising administering a composition comprising milk infant formula and microvesicles isolated from skim fraction of natural milk, wherein the microvesicles encapsulate or comprise miRNA molecules, wherein the miRNA molecules comprise miR-148a and miR-6073, wherein the microvesicles further encapsulate or comprise biologically active compounds, and wherein the composition substantially does not include cells present in natural milk.

* * * * *